(12) United States Patent
Morinaka et al.

(10) Patent No.: US 9,115,079 B2
(45) Date of Patent: Aug. 25, 2015

(54) NDM INHIBITOR

(75) Inventors: Akihiro Morinaka, Kawasaki (JP); Kazunori Maebashi, Yokohama (JP); Takashi Ida, Yokohama (JP); Muneo Hikida, Himeji (JP); Mototsugu Yamada, Kawasaki (JP); Takao Abe, Yokohama (JP)

(73) Assignee: MEIJI SEIKA PHARMA CO., LTD., Tokyo-To (JP)

( * ) Notice: Subject to any disclaimer, the term of this patent is extended or adjusted under 35 U.S.C. 154(b) by 0 days.

(21) Appl. No.: 14/234,456

(22) PCT Filed: Jul. 26, 2012

(86) PCT No.: PCT/JP2012/069050
§ 371 (c)(1),
(2), (4) Date: Mar. 10, 2014

(87) PCT Pub. No.: WO2013/015388
PCT Pub. Date: Jan. 31, 2013

(65) Prior Publication Data
US 2014/0221330 A1 Aug. 7, 2014

(30) Foreign Application Priority Data
Jul. 26, 2011 (JP) ................................. 2011-163599

(51) Int. Cl.
| | |
|---|---|
| *C07C 69/593* | (2006.01) |
| *A61K 45/06* | (2006.01) |
| *A61K 31/194* | (2006.01) |
| *A61K 31/351* | (2006.01) |
| *A61K 31/40* | (2006.01) |
| *A61K 31/407* | (2006.01) |
| *A61K 31/4164* | (2006.01) |
| *C07D 309/06* | (2006.01) |
| *C07C 279/08* | (2006.01) |
| *C07C 217/18* | (2006.01) |
| *C07C 233/65* | (2006.01) |
| *C07C 235/20* | (2006.01) |
| *C07C 237/22* | (2006.01) |
| *A61K 31/216* | (2006.01) |
| *A61K 31/225* | (2006.01) |
| *A61K 31/4015* | (2006.01) |
| *A61K 31/4174* | (2006.01) |
| *A61K 31/4406* | (2006.01) |
| *A61K 31/45* | (2006.01) |
| *A61K 31/5375* | (2006.01) |
| *C07C 69/608* | (2006.01) |
| *C07C 69/612* | (2006.01) |
| *C07C 69/618* | (2006.01) |

(Continued)

(52) U.S. Cl.
CPC ............. *C07C 69/593* (2013.01); *A61K 31/194* (2013.01); *A61K 31/216* (2013.01); *A61K 31/225* (2013.01); *A61K 31/351* (2013.01); *A61K 31/40* (2013.01); *A61K 31/407* (2013.01); *A61K 31/4015* (2013.01); *A61K 31/4164* (2013.01); *A61K 31/4174* (2013.01); *A61K 31/4406* (2013.01); *A61K 31/45* (2013.01); *A61K 31/5375* (2013.01); *A61K 45/06* (2013.01); *C07C 57/13* (2013.01); *C07C 57/26* (2013.01); *C07C 57/30* (2013.01); *C07C 57/42* (2013.01); *C07C 57/48* (2013.01); *C07C 57/50* (2013.01); *C07C 59/46* (2013.01); *C07C 59/64* (2013.01); *C07C 63/66* (2013.01); *C07C 69/608* (2013.01); *C07C 69/612* (2013.01); *C07C 69/618* (2013.01); *C07C 69/732* (2013.01); *C07C 217/18* (2013.01); *C07C 233/65* (2013.01); *C07C 235/20* (2013.01); *C07C 237/22* (2013.01); *C07C 279/08* (2013.01); *C07D 207/12* (2013.01); *C07D 211/46* (2013.01); *C07D 213/55* (2013.01); *C07D 233/64* (2013.01); *C07D 295/108* (2013.01); *C07D 309/06* (2013.01)

(58) Field of Classification Search
CPC .................................................. C07C 69/593
USPC ........................................................ 514/192
See application file for complete search history.

(56) References Cited

FOREIGN PATENT DOCUMENTS

| JP | 2009-040743 | 2/2009 |
|---|---|---|
| WO | 2007/034924 | 3/2007 |

OTHER PUBLICATIONS

Dongeun Yong et al., "Characterization of a New Metallo-β-Lactamase Gene, bla$_{NDA-1}$, and a Novel Erythromycin Esterase Gene Carried on a Unique Genetic Structure in Klebsiella pneumoniae Sequence Type 14 from India", Antimicrobial Agents and Chemotherapy, Dec. 2009, vol. 53, No. 12, pp. 5046-5054.

(Continued)

*Primary Examiner* — Taofiq A Solola
(74) *Attorney, Agent, or Firm* — Wenderoth, Lind & Ponack, L.L.P.

(57) ABSTRACT

An objective of the present invention is to provide a novel NDM (New Delhi metallo-β-lactamase) inhibitor that functions as a drug for restoring the antibacterial activity of β-lactam antibiotics that have been inactivated as a result of decomposition by NDM. According to the present invention, there is provided an NDM inhibitor contains a compound represented by general formula (I):

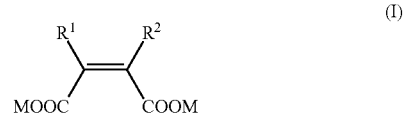

(I)

5 Claims, No Drawings

(51) Int. Cl.

| | |
|---|---|
| C07C 69/732 | (2006.01) |
| C07D 207/12 | (2006.01) |
| C07D 211/46 | (2006.01) |
| C07D 213/55 | (2006.01) |
| C07D 233/64 | (2006.01) |
| C07D 295/108 | (2006.01) |
| C07C 63/66 | (2006.01) |
| C07C 57/13 | (2006.01) |
| C07C 57/26 | (2006.01) |
| C07C 57/30 | (2006.01) |
| C07C 57/42 | (2006.01) |
| C07C 57/48 | (2006.01) |
| C07C 57/50 | (2006.01) |
| C07C 59/46 | (2006.01) |
| C07C 59/64 | (2006.01) |

(56) References Cited

OTHER PUBLICATIONS

Yoshikazu Ishii, "Characteristics of New Delhi metallo-β-lactamas (NDM-1), a novel carbapenem resistance factor", Japanese Journal of Chemotherapy, 2010, vol. 58, No. 6, pp. 639-643, with English translation.

Laurent Poirel et al., "Emergence of Metallo-β-Lactamase NDM-1-Producing Multidrug-Resistant Escherichia coli in Australia", Antimicrobial Agents and Chemotherapy, Nov. 2010, vol. 54, No. 11, pp. 4914-4916.

English translation of Ishii, Y., "Super Saikin no Shinki Yaku Taisei Inshi NMD-1", Medical Bio, vol. 7, No. 6, Nov. 1, 2010, pp. 28-31.

Extended European Search Report issued Feb. 5, 2015 in corresponding European Application No. 12817790.4.

Beiwen Zheng et al., "An unexpected similarity between antibiotic-resistant NDM-1 and beta-lactamase II from Erythrobacter litoralis", Protein & Cell, vol. 2, No. 3, pp. 250-258 (2011).

D.M. Livermore et al., "Activity of carbapenems with ME1071 (disodium 2,3 -diethylmaleate) against Enterobacteriaceae and Acinetobacter spp. with carbapenemases, including NDM enzymes", Journal of Antimicrobial Chemotherapy, vol. 68, No. 1, Sep. 3, 2012, pp. 153-158.

John D Buynak, "β-Lactamase inhibitors: a review of the patent literature (2010-2013)", Expert Opinion on Therapeutic Patents, vol. 23, No. 11, pp. 1469-1481 (2013).

Hope R. et al., "Protection of Carbapenems by ME1071 Against Metallo-62 -Lactamase-Producing Enterobacteriaceae including those with NDM Enzyme", Abstracts Book, Interscience Conference on Antimicrobial Agents & Chemotherapy, American Society for Microbiology, vol. 51, Sep. 17, 2011, presentation No. F1-150.

International Search Report issued Aug. 28, 2012 in International (PCT) Application No. PCT/JP2012/069050.

Ishii, Y., "Super Saikin no Shinki Yakuzai Taisei Inshi NMD-1", Medical Bio, vol. 7, No. 6, Nov. 1, 2010, pp. 28-31, cited in ISR.

NDM INHIBITOR

CROSS-REFERENCE TO RELATED APPLICATIONS

This patent application is based upon and claims the benefit of priority from the prior Japanese Patent Application No. 163599/2011, filed on Jul. 26, 2011, the entire contents of which are incorporated herein by reference.

TECHNICAL FIELD

The present invention relates to an NDM (New Delhi metallo-β-lactamase) inhibitor comprising a maleic acid derivative as active ingredient. Further, the present invention relates to a pharmaceutical composition that, when used in combination with a β-lactam antibiotic in the treatment of bacterial infection, can restore the effectiveness of β-lactam antibiotic against NDM-producing bacteria, and a method for the treatment of bacterial infection.

BACKGROUND ART

NDM has zinc at its active center, is one of metallo-β-lactamases having a broad substrate specificity, and, as with existing metallo-β-lactamases, decomposes β-lactam antibiotics other than monobactam (β-lactam agents.

NDM-1 has been detected for the first time from carbapenem-resistant *Escherichia coli* isolated from a patient transferred from New Delhi in India to Sweden in 2008. At the present time, there are reports about the detection of NDM-1, for example, from bacteria belonging to Enterobacteriaceae such as *Klebsiella pneumoniae* and Gram-negative bacteria such as *Pseudomonas aeruginosa* and *Acinetobacter baumannii* (non-patent document 1). NDM-1 is mainly present on plasmid DNA, and bacteria that have acquired the plasmid are rendered resistant to β-lactam antibiotics. In many cases, the plasmid holds a plurality of drug-resistant genes such as 16S rRNA methylase genes that impart a high level of resistance to aminoglycoside antibiotics and serine-β-lactamases that are monobactam β-lactam degradative enzymes (non-patent document 2).

Accordingly, NDM-1-producing bacteria are in many cases multidrug-resistant, and, thus, difficulties are encountered in the treatment with existing antibacterial agents. Enterobacteriaceae such as *Escherichia coli* are microorganisms causative of diseases that occur even in healthy individuals, such as uncomplicated cystitis. Thus, when NDM-1-producing bacteria spread, there is a possibility that the treatment with antimicrobial agents per se becomes difficult. Existing β-lactamase inhibitors such as clavulanic acid and tazobactam cannot inhibit metallo-β-lactamase such as NDM-1, and, thus, in β-lactam antibiotics that are now on the market, difficulties are encountered in the treatment of infectious diseases induced by NDM-1-producing bacteria (non-patent document 3).

Accordingly, NDM-1 inhibitors have been eagerly desired from the viewpoint of restoring the effectiveness of β-lactam antibiotics such as imipenem against NDM-1-producing bacteria.

Further, the present inventors have found in 2006 metallo-β-lactamase inhibitors that include maleic acid derivatives as active ingredients (patent document 1). In those days, however, there was no report about the isolation of NDM-1, and patent document 1 neither suggests nor discloses the inhibition of NDM-1.

PRIOR ART DOCUMENTS

Patent Document

Patent document 1: WO 2007/034924

Non-Patent Document

Non-patent document 1: Antimicrob. Agents Chemother. vol. 53, No. 12, 5046 (2009)
Non-patent document 2: Japanese Journal of Chemotherapy, vol. 58, No. 6, 639 (2010)
Non-patent document 3: Antimicrob. Agents Chemother. vol. 54, No. 11, 4914 (2010)

SUMMARY OF THE INVENTION

As described above, antibiotics and pharmaceutical compositions effective against NDM-1-producing bacteria have not been found yet, and NDM-1 inhibitors that function to restore the effectiveness of β-lactam antibiotics such as imipenem against NDM-1-producing strains have been eagerly desired.

Thus, an object of the present invention is to provide a novel NDM inhibitor that functions as a drug that suppresses the deactivation of β-lactam antibiotics and can restore antimicrobial activity.

The present inventors have made extensive and intensive studies and, as a result, have found compounds that have inhibitory activity, especially remarkable inhibitory activity against NDM-1, in a group of compounds having a structure of general formula (I) among maleic acid derivatives. The present invention has been made based on this finding.

There are provided the following inventions.

(1) A New Delhi metallo-β-lactamase inhibitor comprising a compound represented by general formula (I), or a salt thereof:

[Chemical formula 1]

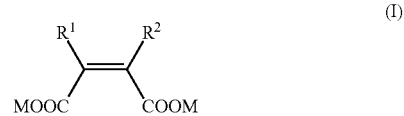

(I)

wherein
$R^1$ represents $C_{1-7}$ alkyl optionally substituted by phenyl or —$OM^1$ wherein $M^1$ represents a hydrogen atom or a pharmaceutically acceptable cation; or tetrahydropyran,
$R^2$ represents $C_{1-7}$ alkyl optionally cyclocondensed with phenyl or optionally substituted by phenyl, pyridyl, or —$OM^1$ wherein $M^1$ represents a hydrogen atom or a pharmaceutically acceptable cation, the phenyl group being optionally substituted by $C_{1-7}$ alkyl, —O—$C_{1-2}$ imidazole, —O-pyrrolidine, —O—$C_{1-2}$—$COOM^2$, —O—$C_{1-2}$—$CONH_2$, —O—$C_{1-2}$—NH—C(=NH)—$NH_2$, —O—$C_{1-7}$ alkyl, —$OM^2$, —$COOM^2$, —$CONH_2$, —CO—$NHCH_2CONH_2$, —CO-morpholine, or —CO-piperidine optionally substituted by hydroxyl, wherein $M^2$ represents a hydrogen atom or a pharmaceutically acceptable cation; tetrahydropyran; or —S—$C_{1-7}$ alkyl, and
two M's which may be the same or different represent a hydrogen atom or a pharmaceutically acceptable cation.

(2) The inhibitor according to (1), wherein the New Delhi metallo-β-lactamase is NDM-1.

(3) The inhibitor according to (1) or (2), which, in combination with a β-lactam antibiotic, is administered simultaneously or sequentially.

(4) The inhibitor according to any one of (1) to (3), which, in combination with a dehydropeptidase inhibitor, is administered simultaneously or sequentially.

(5) A pharmaceutical composition comprising the New Delhi metallo-β-lactamase inhibitor according to any one of (1) to (4) and a pharmaceutically acceptable carrier.

(6) The pharmaceutical composition according to (5), which further comprises a β-lactam antibiotic.

(7) The pharmaceutical composition according to (6), wherein the β-lactam antibiotic is carbapenem antibiotic.

(8) The pharmaceutical composition according to any one of (5) to (7), which further comprises a dehydropeptidase inhibitor.

(9) The pharmaceutical composition according to any one of (5) to (8) for use in the treatment of bacterial infection.

(10) A method for treating bacterial infection, comprising administering a β-lactam antibiotic in combination with the New Delhi metallo-β-lactamase inhibitor according to (1).

(11) The method according to (10), wherein the β-lactam antibiotic is a carbapenem antibiotic.

(12) A compound represented by general formula (II) or a salt thereof:

[Chemical formula 2]

(II)

wherein

R$^3$ represents C$_{3-7}$ cycloalkyl optionally substituted by —OM$^3$ wherein M$^3$ represents a hydrogen atom or a pharmaceutically acceptable cation; or tetrahydropyran, R$^4$ represents C$_{1-7}$ alkyl optionally substituted by phenyl or —OM$^3$ wherein M$^3$ represents a hydrogen atom or a pharmaceutically acceptable cation, the phenyl group being optionally substituted by —O—C$_{1-2}$—NH$_2$, and two M's which may be the same or different represent a hydrogen atom or a pharmaceutically acceptable cation, provided that compounds wherein R$^1$ represents C$_6$ cycloalkyl and R$^2$ represents C$_{1-3}$ alkyl, and compounds wherein R$^1$ represents tetrahydropyran and R$^2$ represents C$_3$ alkyl are excluded.

(13) The compound according to (12) or a salt thereof, which is selected from:

disodium 2-cyclopentyl-3-(cis-4-hydroxycyclohexyl)maleate;

disodium 2,3-bis(cis-4-hydroxycyclohexyl)maleate;

disodium 2,3-bis(tetrahydro-2H-pyran-4-yl)maleate; and disodium 2-(4-(2-aminoethoxy)benzyl)-3-(cis-4-hydroxycyclohexyl)maleate.

Compounds of general formula (I) according to the present invention can inhibit NDM-1 and, as a result, can suppress the deactivation of β-lactam antibiotics and can restore antimicrobial activity.

DETAILED DESCRIPTION OF THE INVENTION

Definition

"C$_{1-7}$," "C$_{1-2}$," or the like as used herein represents the number of carbon atoms unless otherwise specified. For example, "C$_{1-7}$ alkyl" represents alkyl having 1 to 7 carbon atoms. C$_0$ represents a bond.

The term "alkyl" as used herein as a group or a part of a group means straight chain, branched chain, or cyclic alkyl having 1 to 7 carbon atoms unless otherwise specified.

Examples of "alkyl" include methyl, ethyl, n-propyl, i-propyl, n-butyl, i-butyl, s-butyl, t-butyl, n-pentyl, neopentyl, i-pentyl, t-pentyl, n-hexyl, i-hexyl, cyclopropyl, cyclobutyl, cyclopentyl, cyclohexyl, and cycloheptyl.

The term "cycloalkyl" as used herein as a group or a part of a group means monocyclic alkyl having 3 to 7 carbon atoms. Examples of "cycloalkyl" include cyclopropyl, cyclobutyl, cyclopentyl, cyclohexyl, cycloheptyl and the like.

The "pharmaceutically acceptable cations" represent sodium cations, potassium cations, magnesium cations, calcium cations and the like.

New Delhi Metallo-β-Lactamase Inhibitor

According to the present invention, there is provided a New Delhi metallo-β-lactamase inhibitor containing a compound represented by general formula (I) or a salt thereof.

Compounds represented by general formula (I) have New Delhi metallo-β-lactamase inhibitory activity, and these compounds per se can be used as a New Delhi metallo-β-lactamase inhibitor.

As described above, the New Delhi metallo-β-lactamase disadvantageously decomposes many β-lactam antibiotics and deactivates their effectiveness. The combined use of the compounds represented by general formula (I) and β-lactam antibiotics can restore the activity.

Compounds represented by general formula (I) per se can be used as the New Delhi metallo-β-lactamase inhibitor and further is preferably used in combination with β-lactam antibiotics, as a pharmaceutical composition that will be described later.

For example, NDM-1, NDM-2, NDM-3, NDM-4, NDM-5 and the like may be mentioned as the New Delhi metallo-β-lactamase, and NDM-1 is preferred.

General Formula (I)

"C$_{1-7}$ alkyl" represented by R$^1$ may be of any of straight chain, branched chain, and cyclic types and is preferably C$_{1-6}$ alkyl, and examples thereof include methyl, ethyl, n-propyl, i-propyl, n-butyl, i-butyl, s-butyl, t-butyl, n-pentyl, neopentyl, i-pentyl, t-pentyl, n-hexyl, i-hexyl, cyclopropyl, cyclobutyl, cyclopentyl, cyclohexyl, and cycloheptyl. More preferred are methyl, ethyl, n-propyl, i-propyl, n-butyl, i-butyl, s-butyl, t-butyl, cyclopentyl, cyclohexyl, and cycloheptyl.

C$_{1-7}$ alkyl substituted by phenyl and represented by R$^1$ is more preferably —C$_{1-3}$ alkylene-phenyl, and examples thereof include benzyl, phenethyl, and phenylpropyl.

C$_{1-7}$ alkyl that is substituted by —OM$^1$ wherein M$^1$ represents a hydrogen atom or pharmaceutically acceptable cation, and that is represented by R$^1$ is preferably C$_{3-7}$ alkyl substituted by —OM$^1$ wherein M$^1$ represents a hydrogen atom or a pharmaceutically acceptable cation. Examples of such "pharmaceutically acceptable cations" include alkali metals, alkaline earth metals, ammonium, and organic bases. Specific examples thereof include lithium, sodium, potassium, magnesium, calcium, ammonium, ethanolamine, triethanolamine, trimethylamine, triethylamine, and diisopropylamine. Preferred are sodium cations, potassium cations, magnesium cations, and calcium cations. C$_{3-7}$ alkyl substituted by —OM$^1$ wherein M¹ represents a hydrogen atom, a sodium cation, or a potassium cation is preferred, and $C_{3-7}$ alkyl substituted by —OM¹ wherein M¹ represents a hydrogen atom, that is, hydroxyl, is more preferred.

"$C_{1-7}$ alkyl" represented by R² may be of any of straight chain, branched chain, and cyclic types. $C_{1-6}$ alkyl is preferred, and examples thereof include methyl, ethyl, n-propyl, i-propyl, n-butyl, i-butyl, s-butyl, t-butyl, n-pentyl, neopentyl, i-pentyl, t-pentyl, n-hexyl, i-hexyl, cyclopropyl, cyclobutyl, cyclopentyl, cyclohexyl, and cycloheptyl. More preferred are methyl, ethyl, n-propyl, i-propyl, n-butyl, i-butyl, s-butyl, t-butyl, cyclopentyl, cyclohexyl, and cycloheptyl.

$C_{1-7}$ alkyl cyclocondensed with phenyl and represented by R² is phenyl cyclocondensed with cyclic alkyl, and examples thereof include 1H-cyclopropabenzene, 1,2-dihydrocyclobutabenzene, 2,3-dihydro-1H-indene, 1,2,3,4-tetrahydronaphthalene, and 6,7,8,9-tetrahydro-5H-benzo[7]annulene.

$C_{1-7}$ alkyl substituted by phenyl and represented by R² is more preferably —$C_{1-3}$ alkylene-phenyl, and examples thereof include benzyl, phenethyl, and phenylpropyl.

$C_{1-7}$ alkyl substituted by pyridyl and represented by R² is —$C_{1-7}$ alkylene-pyridine, more preferably —$C_{1-3}$ alkylene-pyridine, and examples thereof include pyridinemethyl, pyridineethyl, and pyridinepropyl.

$C_{1-7}$ alkyl that is substituted by —OM¹ wherein M¹ represents a hydrogen atom or a pharmaceutically acceptable cation, and that is represented by R² is preferably $C_{3-7}$ alkyl substituted by —OM¹ wherein M¹ represents a hydrogen atom or a pharmaceutically acceptable cation. Examples of "pharmaceutically acceptable cations" include alkali metals, alkaline earth metals, ammonium, and organic bases. Specific examples thereof include lithium, sodium, potassium, magnesium, calcium, ammonium, ethanolamine, triethanolamine, trimethylamine, triethylamine, and diisopropylamine. Preferred are sodium cations, potassium cations, magnesium cations, and calcium cations. $C_{3-7}$ alkyl substituted by —OM¹ wherein M¹ represents a hydrogen atom, a sodium cation, or a potassium cation is preferred, and $C_{3-7}$ alkyl substituted by —OM¹ wherein M¹ represents a hydrogen atom, that is, hydroxyl, is more preferred.

"—O—$C_{1-7}$ alkyl" represented in the formula in relation to R² may be of any of straight chain, branched chain, and cyclic types, preferably —O—$C_{1-6}$ alkyl, and examples thereof include methoxy, ethoxy, propoxy, isopropoxy, butoxy, isobutoxy, s-butoxy, t-butoxy, cyclopropyloxy, cyclobutyloxy, cyclopentyloxy, and cyclohexyloxy. More preferred are methoxy, ethoxy, propoxy, isopropoxy, t-butoxycyclobutyloxy, cyclopentyloxy, and cyclohexyloxy.

"M²" represented in the formula in relation to R² represents a hydrogen atom or a pharmaceutically acceptable cation. Examples of such "pharmaceutically acceptable cations" include alkali metals, alkaline earth metals, ammonium, and organic bases, and specific examples thereof include lithium, sodium, potassium, magnesium, calcium, ammonium, ethanolamine, triethanolamine, trimethylamine, triethylamine, and diisopropylamine. Preferred are sodium cations, potassium cations, magnesium cations, and calcium cations. M² is preferably a hydrogen atom, a sodium cation, or a potassium cation, more preferably a hydrogen atom or a sodium cation.

"—S—$C_{1-7}$ alkyl" represented by R² is straight chain, branched chain, or cyclic $C_{1-7}$ alkylthio, preferably —S—$C_{1-4}$ alkyl. Examples thereof include methylthio, ethylthio, propylthio, isopropylthio, butylthio, isobutylthio, s-butylthio, and t-butylthio, and more preferred examples thereof include methylthio, ethylthio, propylthio, isopropylthio, and t-butylthio.

M's, which may be the same or different, represent a hydrogen atom or a pharmaceutically acceptable cation.

The pharmaceutically acceptable cation is a cation that can form a salt with one of or both carboxyl groups in general formula (I). Examples thereof include alkali metals, alkaline earth metals, ammonium, and organic bases. Specific examples thereof include lithium, sodium, potassium, magnesium, calcium, ammonium, ethanolamine, triethanolamine, trimethylamine, triethylamine, and diisopropylamine. Sodium cations, potassium cations, magnesium cations, and calcium cations are preferred, sodium cations or potassium cations are more preferred, and sodium cations are particularly preferred.

Compounds in a preferred embodiment of the present invention are compounds of general formula (I) wherein R¹ represents $C_{1-7}$ alkyl that is selected from methyl, ethyl, n-propyl, i-propyl, n-butyl, i-butyl, s-butyl, t-butyl, cyclopentyl, cyclohexyl, and cycloheptyl and is optionally substituted by phenyl or —OM¹ wherein M¹ represents a hydrogen atom, a sodium cation, or a potassium cation; or tetrahydropyran, R² represents $C_{1-7}$ alkyl that is selected from methyl, ethyl, n-propyl, i-propyl, n-butyl, i-butyl, s-butyl, t-butyl, cyclopentyl, cyclohexyl, and cycloheptyl and is optionally cyclocondensed with phenyl or optionally substituted by phenyl, pyridyl, or —OM¹ wherein M¹ represents a hydrogen atom, a sodium cation, or a potassium cation, the phenyl group being optionally substituted by $C_{1-7}$ alkyl, —O—$C_{1-2}$ imidazole, —O-pyrrolidine, —O—$C_{1-2}$—COOM², —O—$C_{1-2}$—CONH₂, —O—$C_{1-2}$—NH₂, —O—$C_{1-2}$—NH—C(=NF)—NH₂, —O—$C_{1-7}$ alkyl, —OM², —COOM², —CONH₂, —CO—NHCH₂CONH₂, —CO-morpholine, or —CO-piperidine optionally substituted by hydroxyl, wherein M² represents a hydrogen atom or a sodium cation; tetrahydropyran; or —S—$C_{1-7}$ alkyl, and two M's which may be the same or different represent a hydrogen atom, a sodium cation, or a potassium cation.

Compounds in a more preferred embodiment of the present invention are compounds of general formula (I) wherein R¹ represents $C_{1-7}$ alkyl that is selected from methyl, ethyl, n-propyl, i-propyl, n-butyl, i-butyl, s-butyl, t-butyl, cyclopentyl, cyclohexyl, and cycloheptyl and is optionally substituted by phenyl or —OM¹ wherein M¹ represents a hydrogen atom; or tetrahydropyran, R² represents $C_{1-7}$ alkyl that is selected from methyl, ethyl, n-propyl, i-propyl, n-butyl, i-butyl, s-butyl, t-butyl, cyclopentyl, cyclohexyl, and cycloheptyl and is optionally cyclocondensed with phenyl or optionally substituted by phenyl, pyridyl, or —OM¹ wherein M¹ represents a hydrogen atom, the phenyl group being optionally substituted by $C_{1-7}$ alkyl, —O—$C_{1-2}$ imidazole, —O-pyrrolidine, —O—$C_{1-2}$—COOM², —O—$C_{1-2}$—CONH₂, —O—$C_{1-2}$—NH₂, —O—$C_{1-2}$—NH—C(=NH)—NH₂, —O—$C_{1-7}$ alkyl, —OM², —COOM², —CONH₂, —CO—NHCH₂CONH₂, —CO-morpholine, or —CO-piperidine optionally substituted by hydroxyl, wherein M² represents a hydrogen atom or a sodium cation; tetrahydropyran; or —S—$C_{1-4}$ alkyl, and two M's represent a sodium cation.

In a preferred embodiment of the present invention, compounds of general formula (I) are compounds represented by general formula (II) that will be described later. Specific examples thereof include disodium 2-cyclopentyl-3-(cis-4-hydroxycyclohexyl)maleate, disodium 2,3-bis(cis-4-hydroxycyclohexyl)maleate, disodium 2,3-bis(tetrahydro-2H-pyran-4-yl)maleate, and disodium 2-(4-(2-aminoethoxy)benzyl)-3-(cis-4-hydroxycyclohexyl)maleate.

Specific examples of compounds of general formula (I) are as follows.

Disodium 2,3-diethylmaleate
Disodium 2,3-di-n-propylmaleate
Disodium 2-benzyl-3-methylmaleate
Disodium 2-benzyl-3-ethylmaleate
Disodium 3-ethyl-2-(4-hydroxy benzyl)maleate
Disodium 2,3-dibenzylmaleate
Disodium 2-benzyl-3-phenethylmaleate
Disodium 2,3-diphenethylmaleate
Disodium 2-isopropyl-3-methylmaleate
Disodium 3-ethyl-2-isopropylmaleate
Disodium 2,3-diisopropylmaleate
Disodium 3-benzyl-2-isopropylmaleate
Disodium 2-isopropyl-3-(2-methylphenyl)methylmaleate
Disodium 2-cyclopentyl-3-ethylmaleate
Disodium 2-cyclopentyl-3-isopropylmaleate
Disodium 3-benzyl-2-cyclopentylmaleate
Disodium 2,3-dicyclopentylmaleate
Disodium 2-(2,3-dihydro-1H-inden-2-yl)-3-isopropylmaleate
Disodium 2-cyclohexyl-3-isopropylmaleate
Disodium 2-(trans-4-hydroxycyclohexyl)-3-isopropylmaleate
Disodium 2-(cis-4-hydroxycyclohexyl)-3-isopropylmaleate
Disodium 3-isopropyl-2-(tetrahydropyran-4-yl)maleate
Disodium 2-isopropyl-3-[(pyridine-3-yl)methyl]maleate
Disodium 3-ethyl-2-isopropylthiomaleate
Trisodium 2-(4-carboxybenzyl)-3-isopropylmaleate
Disodium 2-(4-carbamoylbenzyl)-3-isopropylmaleate
Disodium 2-isopropyl-3-[4-(morpholine-1-carbonyl)benzyl]maleate
Disodium 2-[4-(4-hydroxypiperidine-1-carbonyl)benzyl]-3-isopropylmaleate
Disodium 2-[4-(2-amino-2-oxoethylcarbamoyl)benzyl]-3-isopropylmaleate
Disodium 2-isopropyl-3-(4-methoxy benzyl)maleate
Trisodium 2-(4-oxidobenzyl)-3-isopropylmaleate
Trisodium 2-[4-((carboxylatomethoxy)benzyl]-3-isopropylmaleate
Disodium 2-[4-(2-amino-2-oxoethoxy)benzyl]-3-isopropylmaleate
Disodium 2-[4-(2-aminoethoxy)benzyl]-3-isopropylmaleate
Disodium 2-{4-[2-(1H-imidazol-1-yl)ethoxy]benzyl}-3-isopropylmaleate
Disodium 2-isopropyl-3-[4-(pyrrolidin-3-yloxy)benzyl]maleate
Disodium 2-[4-(2-guanidinoethoxy)benzyl]-3-isopropyl maleate
Disodium 2-cyclopentyl-3-(cis-4-hydroxycyclohexyl)maleate
Disodium 2,3-bis(cis-4-hydroxycyclohexyl)maleate
Disodium 2,3-bis(tetrahydro-2H-pyran-4-yl)maleate
Disodium 2-(4-(2-aminoethoxy)benzyl)-3-(cis-4-hydroxycyclohexyl)maleate Compounds of general formula (I) are particularly preferably the following compounds.
Disodium 3-ethyl-2-isopropylmaleate
Disodium 2-cyclopentyl-3-ethylmaleate
Disodium 2,3-dicyclopentylmaleate
Disodium 2-(trans-4-hydroxycyclohexyl)-3-isopropylmaleate
Disodium 2-cyclopentyl-3-(cis-4-hydroxycyclohexyl)maleate
Disodium 2,3-bis(cis-4-hydroxycyclohexyl)maleate Salts of compounds of general formula (I) are preferably pharmaceutically acceptable salts. Examples of "pharmaceutically acceptable salts" include acid addition salts. Compounds of general formula (I) may be used in the form of salts derived from inorganic or organic acids. Such salts include salts of acetic acid, adipic acid, alginic acid, aspartic acid, benzoic acid, benzene sulfonic acid, bisulfuric acid, butyric acid, citric acid, camphoric acid, camphor sulfonic acid, cyclopentanepropionic acid, digluconic acid, dodecylsulfuric acid, ethanesulfonic acid, fumaric acid, glucoheptanic acid, glycerophosphoric acid, hemisulfuric acid, heptanoic acid, hexanoic acid, hydrochloric acid, hydrobromic acid, hydroiodic acid, 2-hydroxyethanesulfonic acid, lactic acid, maleic acid, methanesulfonic acid, 2-naphthalenesulfonic acid, nicotinic acid, oxalic acid, pamoic acid, pectinic acid, persulfuric acid, 3-phenylpropionic acid, picric acid, pivalic acid, propionic acid, succinic acid, tartaric acid, thiocyanic acid, tosylic acid, and undecanoic acid.

Production of Compounds Represented by General Formula (I)

Compounds represented by general formula (I) can be produced according to the description of a production process and working examples in WO 2007/034924. In particular, compounds of Examples 1 to 37 according to the present invention are publicly known compounds and can be obtained according to Examples 4, 7, 9, 11, 14, 16, 18, 20, 22, 24, 26, 28, 30, 32, 34, 37, 39, 41, 43, 46, 48, 51, 54, 66, 70, 72, 74, 78, 80, 82, 86, 88, 90, 92, 94, 96, and 98 in WO 2007/034924. Compounds of Examples 38 to 41 according to the present invention are novel compounds and can be produced according to the description of WO 2007/034924. Specific production processes are described in working examples that will be described later.

Pharmaceutical Composition

The compounds of the present invention per se are useful and have the effect of inhibiting NDM-1, for example, in the form of pharmaceutically acceptable salts. Further, the compounds of the present invention are drugs that, when used in combination with β-lactam antibiotics, enhance therapeutic effect of bacterial infection in animals and human patients.

Compounds of general formula (I) in the present invention that are maleic acid derivatives, when used in combination with a pharmaceutically acceptable carrier, can be formulated into pharmaceutical compositions. The carrier is a preparation additive which will be described below.

A medicament provided by the present invention is characterized by including as active ingredient a substance selected from the group consisting of a compound represented by general formula (I) and a physiologically acceptable salt thereof, and a hydrate or solvate thereof. The medicament according to the present invention can be orally or parenterally administered. Examples of parenteral administration include administration routes such as intranasal, instillation, ear drop, percutaneous, tracheobronchial, intrarectal, endourological, subcutaneous, intramuscular, and intravenous administration.

The above substance as active ingredient per se may be administered as the medicament according to the present invention. In general, it is preferable that one or more preparation additives (carriers) are used to produce pharmaceutical composition before administration. Examples of pharmaceutical preparations suitable for oral administration include tablets, granules, fine subtilaes, dusts, syrups, solutions, capsules, chewable formulations, or suspensions. Examples of pharmaceutical preparations suitable for parenteral administration include injections, drops, inhalants, sprays, suppositories, pessaries, percutaneous absorption preparations, transmucosal absorption preparations, eye drops, ear drops, nasal drops, or patches. Liquid preparations such as injections or drops may be provided, for example, as lyophilized powdery pharmaceutical compositions and may be dissolved or suspended in water or other suitable media (such as physiolosical saline, glucose infusions, or buffer solutions) before use.

Preparation additives may be properly selected depending upon the form of pharmaceutical compositions, and types of such additives are not particularly limited. Examples thereof include stabilizers, surfactants, plasticizers, lubricants, solubilizers, buffering agents, sweetening agents, bases, adsorbents, corrigents, binders, suspending agents, glossing agents, coating agents, flavors, perfumes, wetting agents, wetting modifiers, fillers, antifoaming agents, masticatories, refrigerants, colorants, sugar coating agents, tonicity adjusting agents, pH adjustors, softeners, emulsifiers, pressure-sensitive adhesives, adhesion enhancing agents, viscous agents, thickening agents, foaming agents, excipients, ispersants, propellants, disintegrators, disintegration assistants, aromatic substances, moistureproof agents, antiseptics, preservatives, soothing agents, solvents, dissolving agents, solubilizers, and fluidizers. They may be used in a combination of two or more of them. Specific examples of these preparation additives are described, for example, in Japanese Pharmaceutical Excipients Directory (edited by International Pharmaceutical Excipients Council Japan, published by Yakuji Nippo, Ltd.). Thus, a person having ordinary skill in the art could select proper preparation additives according to the form of pharmaceutical compositions and could produce pharmaceutical compositions in a desired form according to methods commonly used in the art. In general, the pharmaceutical composition can be prepared so that the content of the above substance in the pharmaceutical composition is 1.0 to 100% (w/w), preferably 1.0 to 60% (w/w).

More specifically, preparation additives usable herein include, but are not limited to, gelatin, lactose, saccharose, titanium oxide, starch, crystalline cellulose, hydroxypropylmethylcellulose, carboxymethylcellulose, corn starch, microcrystalline waxes, white petrolatum, magnesium aluminometasilicate, anhydrous calcium phosphate, citric acid, trisodium citrate, hydroxypropylcellulose, sorbitol, sorbitan fatty acid esters, polyisobate, sucrose fatty acid esters, polyoxyethylene hydrogenated castor oils, polyvinyl pyrrolidone, magnesium setearate, light anhydrous silicic acid, talc, vegetable oils, benzyl alcohol, gum arabic, propylene glycol, polyalkylene glycol, cyclodextrin, or hydroxypropylcyclodextrin.

Regarding the medicament according to the present invention, the dose and the number of times of administration are not particularly limited and may be appropriately determined in consideration of various conditions, for example, the purpose of treatment or prophylaxis, the type of diseases, the age, weight, and severity of condition of patients. For oral administration, the preparation may be administered usually in an amount of about 0.1 to 100 mg/kg/adult in terms of amount of active ingredient at a time daily or divided doses of several times daily. For parenteral administration, preferably, the preparation may be administered usually in an amount of about 0.001 to 100 mg/kg/adult in terms of amount of active ingredient at a time daily or divided doses of several times daily.

Compounds according to the present invention in combination with antibiotics can be used for the treatment of infection included in antibacterial spectra of the antibiotics, as well as for the treatment of infection resulting from New Delhi metallo-β-lactamase-producing strains (particularly NDM-1-producing strains). Examples of NDM-1-producing strains include bacteria belonging to Enterobacteriaceae such as *Escherichia coli* and *Klebsiella pneumoniae* and Gram-negative bacteria such as *Pseudomonas aeruginosa* and *Acinetobacter baumannii*.

Compounds according to the present invention may be properly used in combination with other drugs, and examples of drugs usable in combination the compounds according to the present invention include β-lactam antibiotics and β-lactamase inhibitors. The combined use is useful for the treatment of infection in animals and mammals such as humans.

Carbapenem, penicillin, cephem, or their prodrugs may be mentioned as the β-lactam antibiotic. The use of one or more of the β-lactam antibiotics as a mixture with or in combination with compounds of general formula (I) is useful. In this case, compounds of general formula (I) and β-lactam antibiotics may be administered separately from each other, or alternatively may be administered as a single composition containing both the active ingredients.

Regardless of separate administration or incorporation in the composition according to the present invention, carbapenems, penicillins, cephems, and other β-lactam antibiotics that are suitable for use in combination with compounds of general formula (I) include both antibiotics that are sensitive or resistant to NDM-1.

When compounds of general formula (I) are used in combination with carbapenem antibiotics, these compounds may further be used in combination with dehydropeptidase (DHP) inhibitors. Many carbapenems are already known to be subject to degradation with DHP, and preferred inhibitors are, for example, cilastatin or salts thereof.

Serine-β-lactamase inhibitors such as clavulanic acid, sulbactam, or tazobactam may also be administered in combination with compounds of the present invention and β-lactam antibiotics, separately from or as a mixed preparation with any one of or both the compounds of the present invention and β-lactam antibiotics.

All of clinically usable carbapenems may be mentioned as examples of carbapenems usable in combination with compounds of general formula (I), and examples thereof include imipenem, meropenem, biapenem, dripenem, ertapenem, tebipenem (pivaloyloxymethyl(4R,5S,6S)-6-[(R)-1-hydroxyethyl]-4-methyl-7-oxo-3-{[1-(1,3-thiazolin-2-yl)azetidin-3-yl]thio})-1-azabicyclo[3.2.0]hept-2-ene-2-carboxylate), CS-023((−)-(4R,5S,6S)-3-[[(3S,5S)-5-[(S)-3-(2-guanidinoacetylamino)pyrrolidin-1-ylcarbonyl]-1-methylpyrrolidin-3-yl]thio]-6-[(R)-1-hydroxyethyl]-4-methyl-7-oxo-azabicyclo[3.2.0]hept-2-ene-2-carboxylic acid), and ME1036 ((1S,5R,6S)-2-[7-(1-carbamoylmethylpyridinium-3-yl)carbonylimidazo[5,1-b]thiazol-2-yl]-6-((1R)-1-hydroxyethyl)-1-methyl-1-carbapen-2-em-3-carboxylate).

Penicillins that can be administered in combination with compounds according to the present invention include benzylpenicillin, phenoxymethylpenicillin, carbenicillin, azidocillin, propicillin, ampicillin, amoxicillin, epicillin, ticarcillin, ciclacillin, pirbenicillin, azlocillin, mezlocillin, sulbenicillin, piperacillin, and other publicly known penicillins. These penicillins may be used in their prodrug forms, for example, as intravitally hydrolyzable esters such as acetoxymethyl, pivaioyloxymethyl, 1-(ethoxycarbonyloxy)ethyl, and phthalidyl esters of ampicillin, benzylpenicillin, and amoxycillin, as aldehyde or ketone adducts of penicillins having a 6-α-aminoacetamide side chain (for example, analogous derivatives of hetacillin, metampicillin, and amoxicillin), and as esters (for example, phenyl and indanyl esters) of penicillins having a 6-α-carboxyacetamide side chain (for example, carbenicillin and ticarcillin).

Examples of cephems that can be administered in combination with compounds according to the present invention include cefatrizine, cephaloridine, cephalothin, cefazolin, cephalexin, cefacetrile, cephapirin, cefamandole naphate, cefradine, 4-hydroxycephalexin, cefoperazone, latamoxef, cefminox, flomoxef, cefsulodin, ceftazidime, cefuroxime, cefditoren, cefmetazole, cefotaxime, ceftriaxone, cefepime, cefpirome, cefozopran, and other publicly known cephems. All of them may also be used in their prodrug forms.

Examples of β-lactam antibiotics other than carbapenems, penicillins, and cephems that can be administered in combination with compounds according to the present invention include other publicly known β-lactam antibiotics such as aztreonam, faropenem, and ritipenem. All of them may also be used in their prodrug forms.

Carbapenems particularly suitable for use in combination with compounds according to the present invention include imipenem, meropenem, biapenem, and doripenem.

Penicillins particularly suitable for use in combination with compounds according to the present invention include ampicillin, amoxicillin, carbenicillin, piperacillin, azlocillin, mezlocillin, and ticarcillin. Such penicillins may be used in the form of pharmaceutically acceptable salt such as sodium salts. Ampicillin or amoxicillin may be used in another form, that is, may be used in the form of fine particles of amphoteric ion type for suspensions for injection or suspensions for infusion (ampicillin trihydrate or amoxicillin trihydrate), in combination with compounds of general formula (I).

Cephems particularly suitable for use in combination with compounds according to the present invention include cefotaxime, ceftriaxone, ceftazidime, and cefepime. They may be used in the form of pharmaceutically acceptable salts such as sodium salts.

When compounds of general formula (I) are administered in combination with penicillin, cephem, carbapenem, or other β-lactam antibiotics, the ratio of the amount of compounds of general formula (I) to the amount of the β-lactam antibiotics may be varied in a wide range.

According to the present invention, there is provided use of compounds of general formula (I) or salts thereof, for the manufacture of a medicament for the treatment of bacterial infection.

According to another aspect of the present invention, there is provided a method for treating bacterial infection in humans or animals, comprising administering an NDM-1 inhibitor of general formula (I) in combination with a β-lactam antibiotic. More preferably, the β-lactam agent is carbapenem antibiotic.

According to the present invention, there is provided a pharmaceutical composition comprising an NDM inhibitor of general formula (I) in combination with a β-lactam antibiotic and a pharmaceutically acceptable carrier.

According to the present invention, there is provided a composition comprising an NDM inhibitor of general formula (I) in combination with carbapenem antibiotic and a pharmaceutically acceptable carrier.

The pharmaceutical composition may contain a serine-β-lactamase inhibitor or/and a DHP inhibitor. Serine-β-lactamase inhibitors include clavulanic acid, sulbactam, and tazobactam, and DHP inhibitors include cilastatin and salts thereof.

According to the present invention, there is provided a method for treating infection, comprising administering a compound of general formula (I), a β-lactam antibiotic, and optionally a dehydropeptidase (DHP) inhibitor, simultaneously or successively to animals including humans.

According to the present invention, there is provided use of a compound of general formula (I) for the manufacture of a pharmaceutical composition comprising a β-lactam antibiotic and optionally a dehydropeptidase (DHP) inhibitor, especially for the manufacture of a therapeutic agent for infection.

According to the present invention, there is provided a combination comprising a compound of general formula (I) and a β-lactam antibiotic (preferably carbapenem antibiotic, cephem antibiotic, or penicillin antibiotic, more preferably carbapenem antibiotic). The combination can be used for the treatment of bacterial infection.

According to the present invention, there is provided a kit comprising a compound of general formula (I) and a β-lactam antibiotic (preferably carbapenem antibiotic, cephem antibiotic, or penicillin antibiotic, more preferably carbapenem antibiotic). The kit can be used for the treatment of bacterial infection.

NDM-1 Inhibitory Activity of Compounds of General Formula (I)

NDM-1 inhibitory activity of compounds of general formula (I) was measured. As described and disclosed in Tables 1 and 2 below, all the compounds had a high inhibitory activity of less than 100 μM in terms of $IC_{50}$. In Tables 1 and 2, the inhibitory activity of the compounds was indicated on three levels: A (less than 10 μM), B (10<30 μM), and C (30<100 μM).

Further, the effect of using the compounds according to the present invention in combination with β-lactam antibiotics in NDM-1 producing *E. coli* was identified. As a result, all the compounds restored the activity of β-lactam antibiotic per se by a factor of 2 to 256.

Novel Compounds Represented by General Formula (II)

A group of compounds represented by general formula (I) includes novel compounds. Thus, according to the present invention, novel compounds represented by general formula (II) are provided.

"$C_{3-7}$ cycloalkyl" represented by $R^3$ is a monocyclic alkyl having 3 to 7 carbon atoms, and examples thereof include cyclopropyl, cyclobutyl, cyclopentyl, cyclohexyl, and cycloheptyl. Cyclopentyl or cyclohexyl is preferred.

"$M^3$" represented in the formula in relation to $R^3$ represents a hydrogen atom or a pharmaceutically acceptable cation. Examples of "pharmaceutically acceptable cations" include alkali metals, alkaline earth metals, ammonium, and organic bases. Specific examples thereof include lithium, sodium, potassium, magnesium, calcium, ammonium, ethanolamine, triethanolamine, trimethylamine, triethylamine, and diisopropylamine. For example, sodium cations, potassium cations, magnesium cations, and calcium cations are preferred. Preferably, $M^3$ represents a hydrogen atom, a sodium cation or a potassium cation, more preferably a hydrogen atom.

The "$C_{1-7}$ alkyl" represented by $R^4$ may be of any of straight chain, branched chain, and cyclic types and is preferably $C_{1-6}$ alkyl, and examples thereof include methyl, ethyl, n-propyl, i-propyl, n-butyl, i-butyl, s-butyl, t-butyl, n-pentyl, neopentyl, i-pentyl, t-pentyl, n-hexyl, i-hexyl, cyclopropyl, cyclobutyl, cyclopentyl, cyclohexyl, and cycloheptyl. Methyl, ethyl, n-propyl, i-propyl, n-butyl, i-butyl, s-butyl, t-butyl, cyclopentyl, cyclohexyl, and cycloheptyl are preferred, and cyclopentyl or cyclohexyl is more preferred.

$C_{1-7}$ alkyl substituted by phenyl and represented by $R^4$ is more preferably —$C_{1-3}$ alkylene-phenyl, and examples thereof include benzyl, phenethyl, and phenylpropyl. Benzyl is preferred.

"$M^3$" represented in the formula in relation to $R^4$ represents a hydrogen atom or a pharmaceutically acceptable cation. Examples of "pharmaceutically acceptable cations" include alkali metals, alkaline earth metals, ammonium, and organic bases, and specific examples thereof include lithium, sodium, potassium, magnesium, calcium, ammonium, ethanolamine, triethanolamine, trimethylamine, triethylamine, and diisopropylamine. For example, sodium cations, potassium cations, magnesium cations, and calcium cations are preferred. Preferably, $M^3$ represents a hydrogen atom, a sodium cation, or a potassium cation, more preferably a hydrogen atom.

M's, which may be the same or different, represent a hydrogen atom or a pharmaceutically acceptable cation.

The "pharmaceutically acceptable cation" is a cation that can form a salt with one of or both the carboxyl groups in general formula (II). Examples thereof include alkali metals, alkaline earth metals, ammonium, and organic bases, and specific examples thereof include lithium, sodium, potassium, magnesium, calcium, ammonium, ethanolamine, triethanolamine, trimethylamine, triethylamine, and diisopropylamine. For example, sodium cations, potassium cations, magnesium cations, and calcium cations are preferred, sodium cations or potassium cations are more preferred, and sodium cations are particularly preferred.

Specific examples of compounds of general formula (II) are as follows.
Disodium 2-cyclopentyl-3-(cis-4-hydroxycyclohexyl)maleate
Disodium 2,3-bis(cis-4-hydroxycyclohexyl)maleate
Disodium 2,3-bis(tetrahydro-2H-pyran-4-yl)maleate
Disodium 2-(4-(2-aminoethoxy)benzyl)-3-(cis-4-hydroxycyclohexyl)maleate The following inventions are also provided.

(1) An NDM inhibitor comprising a compound represented by general formula (I):

[Chemical formula 3]

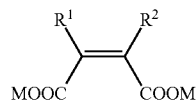

(I)

wherein $R^1$ represents $C_{1-7}$ alkyl and is optionally substituted by phenyl; $R^2$ represents $C_{1-7}$ alkyl optionally cyclocondensed with phenyl or optionally substituted by phenyl, pyridyl, or hydroxyl, the phenyl group being $C_{1-7}$ alkyl, —O—$C_{1-2}$— imidazole, —O-pyrrolidine, —O—$C_{1-2}$—COOM, —O—$C_{1-2}$—CONH$_2$, —O—$C_{1-2}$—NH$_2$, —O—$C_{1-2}$—NH—C(=NH)—NH$_2$, —O—$C_{1-7}$ alkyl, —OM, —COOM, —CONH$_2$, —CO—NHCH$_2$CONH$_2$, —CO-morpholine, or —CO-piperidine optionally substituted by hydroxyl; tetrahydropyran; or —S—$C_{1-7}$ alkyl, and M's represent a hydrogen atom or a pharmaceutically acceptable cation.

(2) The inhibitor according to (1), wherein NDM is NDM-1.

(3) A pharmaceutical composition comprising an NDM inhibitor according to (1) and a pharmaceutically acceptable carrier.

(4) The pharmaceutical composition according to any one of (1) to (3), which may contain a DHP inhibitor.

(5) The pharmaceutical composition according to (3) or (4) which, in combination with a β-lactam antibiotic, is administered simultaneously or successively in a method for the treatment of bacterial infection.

(6) The pharmaceutical composition according to (5), wherein the β-lactam antibiotic is a carbapenem antibiotic.

(7) A method for the treatment of bacterial infection, the method comprising administering a β-lactam antibiotic in combination with an NDM inhibitor according to (1).

(8) The method according to (7), wherein the β-lactam antibiotic is a carbapenem antibiotic.

EXAMPLES

Production Examples

Among compounds of Examples 1 to 41 used, compounds of Examples 1 to 37 are described in WO 2007/034924 and were produced according to Examples 4, 7, 11, 14, 16, 18, 20, 22, 24, 26, 28, 30, 32, 34, 37, 39, 41, 43, 46, 48, 51, 54, 66, 70, 72, 74, 78, 80, 82, 86, 88, 90, 92, 94, 96, and 98. Compounds of Examples 38 to 41 were produced as follows.

Production Example 1

Production of Disodium 2-cyclopentyl-3-(cis-4-hydroxycyclohexyl)maleate (Compound 38

Step 1: Benzyl 2-(1,4-dioxaspiro[4,5]decan-8-ylidene)acetate

Benzyl (triphenylphosphoranylidene)acetate (47.30 g, 115.2 mmol) was added to a solution of 1,4-dioxaspiro[4,5]decan-8-one (10.0 g, 64.02 mmol) in toluene (300 ml) at room temperature, and the mixture was stirred at 95° C. for 48 hr. The reaction mixture was allowed to cool to room temperature, and the solvent was removed by distillation under reduced pressure. The residue was diluted with ether and hexane, the resultant precipitate was removed by filtration, and the filtrate was concentrated. The residue was chromatographed on silica gel column (hexane:ethyl acetate=9:1) to give the title compound as a colorless oil (17.0 g, yield 92%).

1H-NMR (400 MHz, CDCl$_3$): δ (ppm) 7.37-7.30 (m, 5H), 5.73 (s, 1H), 5.14 (s, 2H), 3.98 (s, 4H), 3.02 (t, J=6.8 Hz, 2H), 2.38 (t, J=6.8 Hz, 2H), 1.77 (m, 4H); MS (ESI): m/z 288 (M$^+$).

Step 2: Benzyl 2-(1,4-dioxaspiro[4,5]decan-8-yl)acetate

Diphenyl sulfide (33 mg, 0.18 mmol) and 10% Pd-carbon (1.08 g) were added to a solution of benzyl 2-(1,4-dioxaspiro[4,5]decan-8-ylidene)acetate (5.0 g, 17.34 mmol) in methanol (50 ml) under a nitrogen gas stream, the atmosphere in the system was replaced five times with nitrogen gas, was then filled with hydrogen gas, followed by stirring under a hydrogen gas stream for 5 hr. The catalyst was removed by filtration through Celite pad and was washed with ethanol, and the filtrate was concentrated under reduced pressure to give the title compound as a yellow oil (4.1 g, yield 82%).

1H-NMR (400 MHz, CDCl$_3$): δ (ppm) 7.39-7.30 (m, 5H), 5.12 (s, 2H), 3.93 (s, 4H), 2.29 (d, J=7.2 Hz, 2H), 1.91-1.84 (m, 1H), 1.74-1.72 (m, 4H), 1.59-1.52 (m, 2H), 1.36-1.29 (m, 2H); MS (ESI): m/z 290 (M$^+$).

Step 3: Benzyl 2-(4-oxocyclohexyl)acetate p-Toluene sulfonic acidmonohydrate (207 mg, 1.21 mmol) was added to a mixture composed of benzyl 2-(1,4-dioxaspiro[4,5]decan-8-yl)acetate (7.0 g, 24.11 mmol), acetone (220 ml), and water (10 ml) at room temperature, and the mixture was stirred at 55° C. for 15 hr. The mixture was cooled with ice and was adjusted to pH 5 by the addition of solid sodium bicarbonate. The mixture was concentrated under reduced pressure, and the residue was chromatographed on silica gel column (hexane:ethyl acetate=85:15) to give the title compound as a colorless solid (5.1 g, yield 86%).

1H-NMR (400 MHz, CDCl$_3$): δ (ppm) 7.40-7.31 (m, 5H), 5.14 (s, 2H), 2.38-2.24 (m, 7H), 2.20-2.15 (m, 2H), 2.14-1.13 (m, 2H); MS (ESI): m/z 246 (M$^+$).

Step 4: Benzyl 2-(cis-4-hydroxycyclohexyl)acetate

Benzyl 2-(4-oxocyclohexyl)acetate (5.0 g, 20.3 mmol) was dissolved in methanol (150 ml), NaBH$_4$ (770 mg, 20.3 mmol) was added by portions to the solution at 0° C., and the mixture was stirred for 2 hr. The mixture was concentrated under reduced pressure, followed by separation with ethyl acetate and water. The organic layer was washed with saturated brine and was dried over anhydrous magnesium sulfate, and the filtrate was concentrated under reduced pressure. The residue was chromatographed on silica gel column (hexane:ethyl acetate=85:15) to give the title compound as an oil (900 mg, yield 18%).

1H-NMR (400 MHz, CDCl$_3$): δ (ppm) 7.39-7.31 (m, 5H), 5.12 (s, 2H), 3.98 (br s, 1H), 2.31 (d, J=7.2 Hz, 2H), 1.95-1.84 (m, 1H), 1.73-1.67 (m, 2H), 1.62-1.44 (m, 6H), 1.25 (br s, 1H); MS (ESI): m/z 250 (M+H)$^+$.

Step 5: Benzyl 2-(cis-4-((tert-butyldimethylsilyl)oxy)cyclohexyl)acetate

Imidazole (890 mg, 12.88 mmol) was added to a solution of benzyl 2-(cis-4-hydroxycyclohexyl)acetate (2.0 g, 8.06 mmol) in DMF (25 ml) at room temperature, tert-butylchlorodimethylsilane (1.45 g, 9.67 mmol) was then added thereto, and the mixture was stirred at 65° C. for 15 hr. The mixture was allowed to cool to room temperature and was diluted with water, followed by extraction with ethyl acetate. The organic layer was washed with saturated brine and was dried over anhydrous magnesium sulfate, and the filtrate was concentrated under reduced pressure. The residue was chromatographed on silica gel column (hexane:ethyl acetate=85:15) to give the title compound as an oil (2.5 g, yield 86%).

1H-NMR (400 MHz, CDCl$_3$): δ (ppm) 7.37-7.32 (m, 5H), 5.11 (s, 2H), 3.92 (br s, 1H), 2.28 (d, J=7.2 Hz, 2H), 1.82-1.81 (m, 1H), 1.61-1.60 (m, 2H), 1.45-1.44 (m, 6H), 0.88 (s, 9H), 0.01 (s, 6H); MS (ESI): m/z 363 (M)$^+$.

Step 6: n-Benzyl-benzenesulfonyloxaziridine

A mixture composed of n-benzylidene benzenesulfonamide (5.0 g, 20.40 mmol), benzyltriethylammonium chloride (511 mg, 2.44 mmol), chloroform (20 ml), and saturated sodium bicarbonate (20 ml) was cooled with ice, a solution of 75% m-chloroperbenzoic acid (5.64 g, 24.48 mmol) in chloroform (20 ml) was added dropwise over 30 min, and the mixture was stirred at room temperature for 3 hr. The organic layer was separated, was washed with 10% Na$_2$SO$_3$, saturated sodium bicarbonate, and saturated brine quentially, and was dried over potassium carbonate, and the filtrate was concentrated under reduced pressure to give the title compound as a colorless solid (4.5 g, yield 84%).

1H-NMR (400 MHz, CDCl$_3$): δ (ppm) 8.06 (d, J=7.2 Hz, 2H), 7.76 (t, J=7.2 Hz, 1H), 7.64 (t, J=7.6 Hz, 2H), 7.47-7.38 (m, 5H), 5.49 (s, 1H); MS (ESI): m/z 261 (M−H)$^+$.

Step 7: Benzyl 2-cyclopentylacetate p-Toluene sulfonic acid monohydrate (1.48 g, 7.82 mmol) was added to a solution of cyclopentylacetic acid (10.0 g, 78.2 mmol) and benzyl alcohol (8.42 g, 78.2 mmol) in toluene (100 ml) at room temperature, a Dean-Stark water separator was mounted, and the mixture was refluxed for 4 hr. The mixture was allowed to cool to room temperature and was concentrated under reduced pressure, the residue was dissolved in ether, the solution was washed with saturated sodium bicarbonate and saturated brine and was dried over anhydrous magnesium sulfate, and the filtrate was concentrated under reduced pressure. The residue was chromatographed on silica gel column (hexane:ethyl acetate=97:3) to give the title compound as a light yellow oil (12.0 g, yield 70%).

1H-NMR (400 MHz, CDCl$_3$): δ (ppm) 7.38-7.32 (m, 5H), 5.11 (s, 2H), 2.37 (d, J=7.2 Hz, 2H), 2.31-2.21 (m, 1H), 1.85-1.78 (m, 2H), 1.66-1.50 (m, 4H), 1.20-1.12 (m, 2H).

Step 8: Benzyl-2-cyclopentyl-2-hydroxyacetate

A 1.0 M sodium hexamethyldisilazide solution in THF (27.5 ml, 27.5 mmol) was added to anhydrous THF (30 ml), and the mixture was cooled to −78° C. An anhydrous THF solution (20 ml) of benzyl cyclopentylacetate (5.0 g, 22.90 mmol) was added dropwise to the mixture over 30 min, and the mixture was stirred for additional 30 min. Subsequently, an anhydrous THF solution (20 ml) of n-benzyl-benzenesulfonyloxaziridine (7.18 g, 27.5 mmol) was added dropwise to the mixture at −78° C. over one hr, and the mixture was stirred for additional one hr. The reaction mixture was quenched with saturated ammonium chloride and was extracted with ether. The organic layer was washed with water and saturated brine and was dried over anhydrous magnesium sulfate, and the filtrate was concentrated under reduced pressure. The residue was chromatographed on silica gel column (hexane:ethyl acetate=94:6) to give the title compound as a light yellow oil (3.2 g, yield 60%).

1H-NMR (400 MHz, CDCl$_3$): δ (ppm) 7.38-7.34 (m, 5H), 5.23 (d, J=12.4 Hz, 1H), 5.19 (d, J=12.4 Hz, 1H), 4.17 (dd, J=6.4, 1.6 Hz, 1H), 2.69 (d, J=6.4 Hz, 1H), 2.27-2.22 (m, 1H), 1.74-1.380 (m, 8H); MS (ESI): m/z 235 (M+H)$^+$.

Step 9: Benzyl 2-keto-2-cyclopentylacetate

A Dess-Martinn reagent (5.8 g, 13.67 mmol) was added to a solution of benzyl 2-cyclopentyl-2-hydroxyacetate (2.0 g, 8.54 mmol) in dichloromethane (30 ml) at room temperature, and the mixture was stirred for 15 hr. The reaction mixture was quenched with 10% sodium thiosulfate and extracted with dichloromethane. The organic layer was washed with saturated sodium bicarbonate and saturated brine and was dried over anhydrous magnesium sulfate, and the solvent was removed by distillation under reduced pressure. The residue was chromatographed on silica gel column (hexane:ethyl acetate=95:5) to give the title compound as a light yellow oil (1.8 g, yield 90%).

1H-NMR (400 MHz, CDCl$_3$): δ (ppm) 7.41-7.35 (m, 5H), 5.28 (s, 2H), 3.5-3.44 (m, 1H), 1.90-1.78 (m, 4H), 165-1.60 (m, 4H).

Step 10: Dibenzyl 3-(4-((tert-butyldimethylsilyl)oxy)cyclohexyl-2-cyclopentyl-2-hydroxysuccinate A 2.5 M n-butyllithium solution in hexane (0.85 ml, 2.07 mmol) was added to an anhydrous THF (5.0 ml) solution of diisopropylamine (0.3 ml, 2.20 mmol) at −78° C. under an argon stream. The mixture was brought to 0° C. before stirring for 30 min and was again cooled to −78° C. An anhydrous THF (3.0 ml) of benzyl 2-(cis-4-((tert-butyldimethylsilyl)

oxy)cyclohexyl)acetate (500 mg, 1.37 mmol) was added dropwise at −78° C., and the mixture was stirred for one hr. An anhydrous THF (3.0 ml) solution of benzyl 2-keto-2-cyclopentylacetate (320 mg, 1.37 mmol) cooled to −78° C. was added to the resultant enolate solution through a cannula over 10 min. The mixture was stirred at −78° C. for one hr, and the mixture was quenched with acetic acid, was adjusted to pH 4, and was brought to room temperature. The reaction solvent was removed by distillation under reduced pressure, the residue was diluted with ethyl acetate, the diluted solution was washed with water and saturated brine and was dried over anhydrous magnesium sulfate, and the filtrate was concentrated under reduced pressure. The residue was chromatographed on silica gel column (hexane:ethyl acetate=92:8) to give the title compound as low polar diastereomer (180 mg, yield 22%) and high polar diastereomer (220 mg, yield 26%).

Low polar diastereomer: 1H-NMR (400 MHz, CDCl$_3$): δ (ppm) 7.32-7.28 (m, 10H), 5.18 (d, J=12.4 Hz, 1H), 5.06 (d, J=12.4 Hz, 1H), 4.93 (d, J=12.4 Hz, 1H), 4.82 (d, J=12.4 Hz, 1H), 3.95 (s, 1H), 3.81 (s, 1H), 2.92 (d, J=1.6 Hz, 1H), 2.35-2.30 (m, 1H), 2.00-1.92 (m, 2H), 1.80-1.62 (m, 4H), 1.49-1.40 (m, 10H), 0.85 (s, 9H), 0.01 (s, 6H); MS (ESI): m/z 596 (M+H)$^+$.

High polar diastereomer: 1H-NMR (400 MHz, CDCl$_3$): δ (ppm) 7.39-7.34 (m, 10H), 5.25 5.20 (m, 3H), 5.02 (d, J=12.4 Hz, 1H), 3.87 (s, 1H), 3.78 (s, 1H), 2.88 (d, J=4.4 Hz, 1H), 2.30-2.22 (m, 1H), 1.76-1.27 (m, 16H), 0.87 (s, 9H), 0.02 (s, 6H); MS (ESI): m/z 596 (M+H)$^+$.

Step 11: 3-(4-((tert-Butyldimethylsilyl)oxy)cyclohexyl-2-cyclopentyl-2-hydroxysuccinic acid To a solution of a diastereomeric mixture (330 mg, 0.55 mmol) of dibenzyl 3-(4-((tert-butyldimethylsilyl)oxy)cyclohexyl-2-cyclopentyl-2-hydroxysuccinate in ethanol (10 ml) was added 10% Pd carbon (150 mg) under a nitrogen gas stream. The atmosphere in a reaction vessel for the mixture was replaced five times with nitrogen gas, the reaction vessel was filled with hydrogen gas, and the contents of the reaction vessel were stirred for 24 hr under a hydrogen gas stream. The catalyst was collected by filtration through Celite pad and was washed with ethanol, and the filtrate was concentrated under reduced pressure to give the title compound as a colorless solid (190 mg, yield 83%).

1H-NMR (400 MHz, DMSO-D6): δ (ppm) 12.75 (br s, 1H), 12.20 (br s, 1H), 3.96 (br s, 1H), 3.82-3.78 (m, 2H), 3.51-3.46 (m, 2H), 2.63-2.61 (m, 4H), 2.27 (br s, 2H), 1.90-1.37 (m, 10H), 0.90 (s, 9H), 0.07 (s, 6H); MS (ESI): m/z 413 (M−H)$^+$.

Step 12: 3-(cis-4-((tert-Butyldimethylsilyl)oxy)cyclohexyl)-4-cyclopentylfuran-2,5-dione 3-(4-((Tert-butyldimethylsilyl)oxy)cyclohexyl-2-cyclopentyl-2-hydroxysuccinic acid (190 mg, 0.46 mmol) was dissolved in acetic anhydride (7.0 ml), and the mixture was stirred at 130° C. for 15 hr. The mixture was allowed to cool, and excess acetic anhydride was concentrated under reduced pressure, and the residue was chromatographed on silica gel column (hexane:ethyl acetate=95:5) to give the title compound as a light yellow compound (65 mg, yield 37%).

1H-NMR (400 MHz, CDCl$_3$): δ (ppm): 4.06 (br s, 1H), 3.25-3.14 (m, 1H), 2.71-2.64 (m, 1H), 2.22-2.12 (m, 2H), 1.92-1.84 (m, 6H), 1.78-1.75 (m, 2H), 1.67-1.66 (m, 2H), 1.50-1.42 (m, 4H), 0.92 (s, 9H), 0.05 (s, 6H); MS (ESI): m/z 379 (M+H)$^+$.

Step 13: 3-Cyclopentyl-4-(cis-4-hydroxycyclohexyl) furan-2,5-dione

A catalytic amount of concentrated hydrochloric acid was added to a solution of 3-(cis-4-((tert-butyldimethylsilyl)oxy) cyclohexyl)-4-cyclopentylfuran-2,5-dione (65 mg, 0.17 mmol) in ethanol (3.0 ml) at room temperature, and the mixture was stirred at 50° C. for 5 hr. The reaction mixture was allowed to cool and was then concentrated under reduced pressure. The residue was chromatographed on silica gel column (hexane:ethyl acetate=80:20) to give the title compound as a colorless solid (40 mg, yield 88%).

1H-NMR (400 MHz, CDCl$_3$): δ (ppm) 4.14-4.12 (m, 1H), 3.12-3.04 (m, 1H), 2.71-2.63 (m, 1H), 2.23-2.12 (m, 2H), 1.92-1.84 (m, 8H), 1.70-1.65 (m, 2H), 1.62-1.55 (m, 2H), 1.50-1.44 (m, 2H), 1.31 (d, J=3.6 Hz, 1H); MS (ESI): m/z 263 (M−H)$^+$.

Step 14: Disodium 2-cyclopentyl-3-(cis-4-hydroxycyclohexyl)maleate

A 1 M NaOH (0.3 ml, 0.30 mmol) was added to a solution of 3-cyclopentyl-4-(cis-4-hydroxycyclohexyl)furan-2,5-dione (40 mg, 0.15 mmol) in 1,4-dioxane (1.0 ml) at room temperature, and the mixture was stirred for 3 hr. The reaction mixture was concentrated, and the residue was dried in vacuo to give the title compound as a colorless solid (50 mg, quantitative).

1H-NMR (400 MHz, D2O): δ (ppm) 4.02 (br s, 1H), 2.79-2.72 (m, 1H), 2.46-2.40 (m, 1H), 1.80-1.46 (m, 16H); MS (ESI): m/z 281 (M−2Na).

Production Example 2

Production of Disodium 2,3-bis(cis-4-hydroxycyclohexyl)maleate (Compound 39)

Step 1: Benzyl 2-(cis-4-((tert-butyldimethylsilyl) oxy)cyclohexyl)-2-hydroxyacetate A 1.0 M sodium bistrimethylsilylamide solution in THF (3.3 ml, 3.25 mmol) was added to anhydrous THF (5.0 ml), and the mixture was cooled to −78° C. A solution of benzyl 2-(cis-4-((tert-butyldimethylsilyl)oxy)cyclohexyl)acetate (1.0 g, 2.76 mmol) in anhydrous THF (10 ml) was added dropwise to the mixture over 20 min. The mixture was stirred at −78° C. for 30 min, and a solution of n-benzyl-benzenesulfonyloxaziridine (860 mg, 3.25 mmol) in anhydrous THF (7 ml) was added dropwise over 30 min. The mixture was stirred at −78° C. for one hr, was quenched with a saturated aqueous ammonium chloride solution, and was extracted with ether. The organic layer was washed with water and saturated brine, was dried over anhydrous magnesium sulfate, and the filtrate was concentrated under reduced pressure. The residue was chromatographed on silica gel column (hexane: ethyl acetate=93:7) to give the title compound as a yellow oil (650 mg, yield 63%).

1H-NMR (400 MHz, CDCl$_3$): δ (ppm) 7.37-7.36 (m, 5H), 5.25 (d, J=12 Hz, 1H), 5.17 (d, J=12 Hz, 1H) 4.07 (dd, J=7.2, 2.8 Hz, 2H), 3.95 (br s, 1H), 2.60 (d, J=6.8 Hz, 1H), 1.71-1.65 (m, 4H) 1.43-1.26 (m, 4H), 0.87 (s, 9H), 0.01 (s, 6H); MS (ESI): m/z 379 (M+H)$^+$.

Step 2: Benzyl 2-(cis-4-((tert-butyldimethylsilyl) oxy)cyclohexyl)-2-oxoacetate

A Dess-Martin reagent (1.2 g, 2.76 mmol) was added to a solution of benzyl 2-(cis-4-((tert-butyldimethylsilyl)oxy)cyclohexyl)-2-hydroxyacetate (650 mg, 1.72 mmol) in dichloromethane (10 ml) at room temperature, and the mixture was stirred at room temperature for 15 hr. The reaction mixture was quenched with 10% sodium thiosulfate and was extracted with dichloromethane. The organic layer was washed with a saturated aqueous sodium bicarbonate solution, was washed with saturated brine, and was dried over anhydrous magnesium sulfate, and the filtrate was concentrated under reduced pressure. The residue was chromatographed on silica gel column (hexane:ethyl acetate=95:5) to give the title compound as a yellow oil (450 mg, yield 69%).

1H-NMR (400 MHz, CDCl$_3$): δ (ppm) 7.41-7.35 (m, 5H), 5.28 (s, 2H), 3.95 (br s, 1H), 3.03-2.96 (m, 1H), 1.87-1.81 (m, 2H) 1.72-1.62 (m, 4H), 1.54-1.49 (m, 2H), 0.87 (s, 9H), 0.02 (s, 6H); MS (ESI): m/z 377 (M+H)$^+$.

Step 3: Dibenzyl 2,3-bis(cis-4-((tert-butyldimethylsilyl)oxy)cyclohexyl)-2-hydroxysuccinate A 2.5 M n-butyllithium solution in hexane (0.85 ml, 2.07 mmol) was added to a solution of diisopropylamine (0.23 ml, 2.21 mmol) at −78° C. under an argon stream. The mixture was brought to 0° C., was stirred for 30 min, and was again cooled to −78° C. A solution of benzyl 2-(cis-4-((tert-butyldimethylsilyl)oxy)cyclohexyl)acetate (500 mg, 1.37 mmol) in anhydrous THF (5.0 ml) was added dropwise at −78° C., and the mixture was stirred for additional one hr. A solution of benzyl 2-(cis-4-((tert-butyldimethylsilyl)oxy)cyclohexyl)-2-oxoacetate (467 mg, 1.25 mmol) in anhydrous THF (5.0 ml) cooled to −78° C. was added to the resultant enolate solution through a cannula over 10 min. The mixture was stirred at −78° C. for one hr, and the mixture was quenched with acetic acid, was adjusted to pH 4, and was brought to room temperature. The reaction solvent was removed by distillation under reduced pressure, and the residue was diluted with ethyl acetate, and the diluted solution was washed with water and saturated brine and was dried over anhydrous magnesium sulfate, and the filtrate was concentrated under reduced pressure. The residue was chromatographed on silica gel column (hexane:ethyl acetate=95:5) to give the title compound as a colorless solid (500 mg, yield 50%).

1H-NMR (400 MHz, CDCl$_3$): δ (ppm) 7.39-7.35 (m, 10H), 5.20-4.97 (m, 4H), 4.84 (s, 1H), 3.95-3.87 (m, 3H), 2.89-2.87 (m, 1H), 1.75-1.35 (m, 12H), 1.18-1.03 (m, 4H), 0.98 (s, 9H), 0.84 (s, 9H), 0.04 (s, 6H), 0.02 (s, 6H); MS (ESI): m/z 739 (M$^+$).

Step 4: 2,3-Bis(cis-4-((tert-butyldimethylsilyl)oxy)cyclohexyl)-2-hydroxysuccinic acid To a solution of dibenzyl 2,3-bis(cis-4-((tert-butyldimethylsilyl)oxy)cyclohexyl)-2-hydroxysuccinate (500 mg, 0.38 mmol) in ethanol (15 ml) was added 10% Pd-carbon (150 mg) under a nitrogen gas stream. The atmosphere in the reaction vessel was replaced five times with nitrogen gas and was filled with hydrogen gas, and the contents in the reaction vessel were stirred under a hydrogen gas stream for 24 hr. The catalyst was collected by filtration through Celite pad and was washed with ethanol (50 ml×2). The filtrate was concentrated under reduced pressure to give the title compound as a colorless solid (275 mg, yield 73%).

1H-NMR (400 MHz, DMSO-D6): δ (ppm) 12.71 (br s, 1H), 12.30 (br s, 1H), 4.84 (s, 1H), 5.05 (br s, 1H), 3.97 (br s, 1H), 3.51-3.46 (m, 1H), 2.79-2.77 (m, 1H), 1.72-1.28 (m, 16H), 0.99 (s, 9H), 0.89 (s, 9H), 0.06 (s, 6H), 0.04 (s, 6H); MS (ESI): m/z 557 (M−H)$^+$.

Step 5: 2,3-Bis(cis-4-((tert-butyldimethylsilyl)oxy)cyclohexyl)furan-2,5-dione 2,3-Bis(cis-4-((tert-butyldimethylsilyl)oxy)cyclohexyl)-2-hydroxysuccinic acid (270 mg, 0.49 mmol) was dissolved in acetic anhydride (5.0 ml), and the solution was stirred at 120° C. for 24 hr. The mixture was allowed to cool, and excess acetic anhydride was concentrated under reduced pressure. The residue was chromatographed on silica gel column (hexane:ethyl acetate=95:5) to give the title compound as a colorless solid (105 mg, yield 41%).

1H-NMR (400 MHz, CDCl$_3$): δ (ppm) 4.05 (br s, 2H), 2.82-2.74 (m, 2H), 2.29-2.18 (m, 4H) 1.78-1.75 (m, 4H), 1.50-1.38 (m, 8H), 0.94 (s, 18H), 0.06 (s, 12H).

Step 6: 2,3-Bis(cis-4-hydroxycyclohexyl)furan-2,5-dione

A catalytic amount of concentrated hydrochloric acid was added to a solution of 2,3-bis(cis-4-((tert-butyldimethylsilyl)oxy)cyclohexyl)furan-2,5-dione (100 mg, 0.20 mmol) in ethanol (10.0 ml) at room temperature, and the mixture was stirred at 50° C. for 15 hr. The reaction mixture was allowed to cool and was concentrated under reduced pressure. The residue was chromatographed on silica gel column (hexane:ethyl acetate=50:50) to give the title compound as a colorless solid (38 mg, yield 68%).

1H-NMR (400 MHz, CDCl$_3$): δ (ppm) 4.04 (br s, 2H), 2.86-2.79 (m, 2H), 2.29-2.28 (m, 4H), 1.88 (d, J=14.8 Hz, 4H), 1.62 (t, J=13.6 Hz, 4H), 1.44 (d, J=11.2 Hz, 4H); MS (ESI): m/z 293 (M−H)$^+$.

Step 7: Disodium 2,3-bis(cis-4-hydroxycyclohexyl)maleate

A 1 M NaOH (0.2 ml, 0.21 mmol) was added to a solution of 2,3-bis(cis-4-hydroxycyclohexyl)furan-2,5-dione (30 mg, 0.11 mmol) in 1,4-dioxane (1.0 ml) at room temperature, and the mixture was stirred for 3 hr. The reaction mixture was concentrated, and the residue was dried in vacuo to give the title compound as a colorless solid (35 mg, quantitative).

1H-NMR (400 MHz, D2O): δ (ppm) 4.03 (br s, 2H), 2.43-2.38 (m, 2H), 1.82-1.58 (m, 12H), 1.47 (d, J=10.8 Hz, 4H); MS (ESI): m/z 311 (M−2Na)$^+$.

Production Example 3

Production of Disodium 2,3-bis(tetrahydro-2H-pyran-4-yl)maleate (Compound 40)

Step 1: Ethyl 2-(2H-pyran-4(3H,5H,6H)-ylidene)acetate

Triethyl phosphonoacetate (22.6 g, 99.88 mmol) was added to a solution of dihydro-2H-pyran-4(3H)-one (10.0 g, 99.88 mmol) in DMF (100 ml) at room temperature, and the mixture was stirred at 80° C. for 15 hr. The mixture was allowed to cool to room temperature, was diluted with water, and was extracted with ether. The organic layer was washed with water and saturated brine, was dried over anhydrous magnesium sulfate, and the filtrate was concentrated under reduced pressure. The residue was chromatographed on silica gel column (hexane:ethyl acetate=95:5) to give the title compound as a yellow oil (13.2 g, yield 78%).

1H-NMR (400 MHz, CDCl$_3$): δ (ppm) 5.68 (t, J=1.2 Hz, 1H), 4.15 (q, J=7.2 Hz, 2H), 3.79-3.70 (m, 4H), 3.03-3.00 (m, 2H), 2.35-2.32 (m, 2H), 1.28 (t, J=7.2 Hz, 3H); MS (ESI): m/z 170 (M$^+$).

Step 2: Ethyl 2-(tetrahydro-2H-pyran-4-yl)acetate

To a mixture composed of ethyl 2-(2H-pyran-4(3H,5H,6H)-ylidene)acetate (10 g, 58.75 mmol) and ammonium formate (37 g, 587.54 mmol) in methanol (150 ml) was added 10% Pd-carbon (1.0 g) at room temperature, and the mixture was stirred at 70° C. for 15 hr. The reaction mixture was allowed to cool to room temperature, and the catalyst was collected by filtration through Celite pad and was washed with methanol. The filtrate was concentrated under reduced pressure, and the residue was chromatographed on silica gel column (hexane:ethyl acetate=94:6) to give the title compound as an oil (7.9 g, yield 78%).
1H-NMR (400 MHz, CDCl$_3$): δ (ppm) 4.13 (q, J=7.2 Hz, 2H), 3.97-3.93 (m, 2H), 3.44-3.38 (m, 2H), 2.24 (d, J=7.2 Hz, 2H), 2.08-1.92 (m, 1H) 1.66-1.62 (m, 2H), 1.40-1.29 (m, 2H), 1.26 (t, J=7.2 Hz, 3H); MS (ESI): m/z 172 (M$^+$).

Step 3: Benzyl 2-(tetrahydro-2H-pyran-4-yl)acetate

A solution of sodium hydroxide (15.9 g, 44.06 mmol) in water (150 ml) was added dropwise to a solution of ethyl 2-(tetrahydro-2H-pyran-4-yl)acetate (15 g, 8.81 mmol) in methanol (150 ml) at a temperature of 0° C. or below, and the mixture was stirred at room temperature for 15 hr. The solvent of the reaction mixture was removed by distillation under reduced pressure, and the water layer was adjusted to pH 3 by the addition of 1 M hydrochloric acid and was extracted with ethyl acetate. The organic layer was washed with saturated brine and was dried over anhydrous sodium sulfate, and the filtrate was concentrated under reduced pressure to give a corresponding acid as a colorless solid (12.0 g, 94%). This compound was used in the next step without further purification. Benzyl bromide (14.3 g, 83.33 mmol) was added dropwise to a suspension of this compound (10.0 g, 69.44 mmol) and anhydrous potassium carbonate (28.8 g, 208.3 mmol) in acetonitrile (100 ml) at room temperature, and the mixture was refluxed for 48 hr. The solvent of the mixture was removed by distillation under reduced pressure, the residue was diluted with water and was extracted with dichloromethane, and the organic layer was dried over anhydrous sodium sulfate. The filtrate was concentrated under reduced pressure, and the residue was chromatographed on silica gel column (hexane:ethyl acetate=9:1) to give the tile compound as an oil (12.0 g, yield 75%).
1H-NMR (400 MHz, CDCl$_3$): δ (ppm) 7.39-7.34 (m, 5H), 5.12 (s, 2H), 3.95-3.92 (m, 2H), 3.42-3.36 (m, 2H), 2.30 (d, J=7.2 Hz, 2H), 2.09-1.99 (m, 1H) 1.64-1.61 (m, 2H), 1.39-1.29 (m, 2H); MS (ESI): m/z 234 (M$^+$).

Step 4: Benzyl 2-hydroxy-2-(tetrahydro-2H-pyran-4-yl)acetate

A 1.0 M sodium bistrimethylsilylamide solution in THF (13.0 ml, 12.82 mmol) was added to anhydrous THF (15 ml), and the mixture was cooled to −78° C. A solution of benzyl 2-(tetrahydro-2H-pyran-4-yl)acetate (2.5 g, 10.68 mmol) in anhydrous THF (20 ml) was added dropwise to the mixture over 30 min. The mixture was stirred at −78° C. for one hr, and a solution of n-benzyl-benzenesulfonyloxaziridine (3.35 g, 12.82 mmol) in anhydrous THF (30 ml) was added dropwise thereto over one hr. The mixture was stirred at −78° C. for one hr, was quenched with saturated ammonium chloride, and was extracted with ether. The organic layer was washed with water and saturated brine and was dried over anhydrous magnesium sulfate, and the filtrate was concentrated under reduced pressure. The residue was chromatographed on silica gel column (hexane:ethyl acetate=8:2) to give the title compound as an oil (2.1 g, yield 78%).
1H-NMR (400 MHz, CDCl$_3$): δ (ppm) 7.40-7.35 (m, 5H), 5.23 (s, 2H), 4.08 (dd, J=6.0, 4.0 Hz, 1H), 4.01-3.94 (m, 2H), 3.39-3.28 (m, 2H), 2.74 (d, J=6.0 Hz, 1H), 2.01-1.92 (m, 1H) 1.72-1.50 (m, 4H).

Step 5: Benzyl 2-oxo-2-(tetrahydro-2H-pyran-4-yl)acetate

A Dess-Martinn reagent (5.7 g, 13.44 mmol) was added to a solution of benzyl 2-hydroxy-2-(tetrahydro-2H-pyran-4-yl)acetate (2.1 g, 8.404 mmol) in dichloromethane (50 ml) at room temperature, and the mixture was stirred for 15 hr. The reaction mixture was quenched with 10% sodium thiosulfate and was extracted with dichloromethane. The organic layer was washed with a saturated aqueous sodium bicarbonate solution and saturated brine and was dried over anhydrous magnesium sulfate, and the solvent was removed by distillation under reduced pressure. The residue was chromatographed on silica gel column (hexane:ethyl acetate=9:1) to give the title compound as a light yellow oil (1.8 g, yield 90%).
1H-NMR (400 MHz, CDCl$_3$): δ (ppm) 7.41-7.36 (m, 5H), 5.29 (s, 2H), 4.01-3.97 (m, 2H), 3.51-3.44 (m, 2H), 3.31-3.24 (m, 1H) 1.83-1.79 (m, 2H), 1.74-1.63 (m, 2H); MS (ESI): m/z 248 (M$^+$).

Step 6: Dibenzyl 2-hydroxy-2,3-bis(tetrahydro-2H-pyran-4-yl)succinate

A 2.5 M n-butyllithium solution in hexane (5.2 ml, 12.83 mmol) was added to a solution of diisopropylamine (1.9 ml, 13.68 mmol) in anhydrous THF (10.0 ml) at −78° C. under an argon stream. The mixture was brought to 0° C., was stirred for 30 min, and was again cooled to −78° C. A solution of benzyl 2-(tetrahydro-2H-pyran-4-yl)acetate (2.0 g, 8.55 mmol) in anhydrous THF (153.0 ml) was added dropwise thereto at −78° C., and the mixture was stirred for additional one hr. A solution of benzyl 2-oxo-2-(tetrahydro-2H-pyran-4-yl)acetate (2.1 g, 8.55 mmol) in anhydrous THF (20.0 ml) that had been cooled to −78° C. was added to the resultant enolate solution through a cannula over 30 min. The mixture was stirred at −78° C. for one hr, was quenched and adjusted to pH 4 with acetic acid, and was brought to room temperature. The reaction solvent was removed by distillation under reduced pressure, the residue was diluted with ethyl acetate, and the diluted solution was washed with water and saturated brine and was dried over anhydrous magnesium sulfate, and the filtrate was concentrated under reduced pressure. The residue was chromatographed on silica gel column (hexane:ethyl acetate=92:8) to give the title compound as a colorless solid (2.0 g, yield 49%).
1H-NMR (400 MHz, CDCl$_3$): δ (ppm) 7.38-7.28 (m, 10H), 5.27 (d, J=12 Hz, 1H), 5.15 (d, J=12 Hz, 1H), 5.02 (d, J=12 Hz, 1H), 4.96 (d, J=12 Hz, 1H), 3.95-3.69 (m, 6H), 3.39-3.31 (m, 2H), 3.18-3.05 (m, 2H), 2.96-2.85 (m, 2H), 2.04-1.67 (m, 4H), 1.33-1.21 (m, 4H); MS (ESI): m/z 483 (M+H)$^+$.

Step 7: 2-Hydroxy-2,3-bis(tetrahydro-2H-pyran-4-yl)succinic acid

To a solution of dibenzyl 2-hydroxy-2,3-bis(tetrahydro-2H-pyran-4-yl)succinate (2.0 g, 4.15 mmol) in ethanol (50 ml) was added 10% Pd-carbon (300 mg) under a nitrogen atmosphere. The atmosphere in the system was replaced five times with nitrogen gas and was filled with hydrogen gas, and the system was stirred under a hydrogen atmosphere for 24 hr. The catalyst was collected by filtration through Celite pad and was washed with ethanol. The filtrate was concentrated under reduced pressure to give the title compound as a colorless solid (1.2 g, yield 96%).

1H-NMR (400 MHz, DMSO-D6): δ (ppm) 12.8 (br s, 2H), 3.88-3.79 (m, 4H), 3.47-3.41 (m, 1H), 3.35-3.13 (m, 4H) 2.69-2.66 (m, 1H), 2.07-1.94 (m, 1H), 1.85-1.04 (m, 8H); MS (ESI): m/z 301 (M−H)$^+$.

Step 8: 3,4-Bis(tetrahydro-2H-pyran-4-yl)furan-2,5-dione

2-Hydroxy-2,3-bis(tetrahydro-2H-pyran-4-yl)succinic acid (1.2 g, 3.98 mmol) was dissolved in acetic anhydride (15 ml), and the solution was stirred at 120° C. for 24 hr. Excess acetic anhydride in the reaction mixture was removed by distillation under reduced pressure, and the residue was chromatographed on silica gel column (hexane:ethyl acetate=40:60) to give the title compound as a colorless solid (0.6 g, yield 60%).

1H-NMR (400 MHz, CDCl$_3$): δ (ppm) 4.09 (dd, J=15.2, 9.6 Hz, 4H) 3.48 (dt, J=12.4, 2.0 Hz, 4H), 3.04-2.96 (m, 2H), 2.24-2.13 (m, 4H), 1.53 (dd, J=12.8, 2.0 Hz, 4H); MS (ESI): m/z 265 (M−H)$^+$.

Step 9: Disodium 2,3-bis(tetrahydro-2H-pyran-4-yl)maleate

A 1 M NaOH (4.5 ml, 4.5 mmol) was added to a solution of 3,4-bis(tetrahydro-2H-pyran-4-yl)furan-2,5-dione (600 mg, 2.25 mmol) in 1,4-dioxane (4.5 ml) at room temperature, and the mixture was stirred for 24 hr. The reaction mixture was concentrated, and the residue was dried in vacuo to give the title compound as a colorless solid (0.7 g, quantitative).

1H-NMR (400 MHz, D2O): δ (ppm) 3.98 (dd, J=11.2, 3.6 Hz, 4H) 3.53 (t, J=11.2 Hz, 4H), 2.71-2.65 (m, 2H), 1.82-1.72 (m, 4H), 1.59-1.56 (m, 4H); MS (ESI): m/z 283 (M−2Na)$^+$.

Production Example 4

Production of Disodium 2-(4-(2-aminoethoxy)benzyl)-3-(cis-4-hydroxycyclohexyl)maleate (Compound 41)

Step 1: Benzyl 3-(4-hydroxyphenyl)propanoate

Benzyl bromide (5.7 g, 33.09 mmol) was added to a suspension of 3-(4-hydroxyphenyl)propanoic acid (5.0 g, 30.08 mmol) and anhydrous potassium carbonate (8.31 g, 60.17 mmol) in anhydrous DMF (60 ml), and the mixture was stirred for 15 hr. The reaction mixture was diluted with water and was extracted with ethyl acetate, and the organic layer was washed with saturated brine and was dried over anhydrous sodium sulfate. The filtrate was concentrated under reduced pressure, and the residue was chromatographed on silica gel column (hexane:ethyl acetate=8:2) to give the title compound as an oil (6.8 g, yield 88%).

1H-NMR (400 MHz, CDCl$_3$): δ (ppm) 7.38-7.28 (m, 5H), 7.03 (d, J=8.8 Hz, 2H), 6.73 (d, J=9.2 Hz, 2H), 5.10 (s, 2H), 4.90 (s, 1H), 2.89 (t, J=7.2 Hz, 2H), 2.65 (t, J=7.2 Hz, 2H).

Step 2: Benzyl 3-(4-((tert-butyldimethylsilyl)oxy)phenyl)propanoate

A solution of benzyl 3-(4-hydroxyphenyl)propanoate (1.0 g, 11.70 mmol) in dichloromethane (60 ml) was cooled to 0° C., and imidazole (1.30 g, 18.73 mmol) and tert-butylchlorodimethylsilane (1.94 g, 12.87 mmol) were added thereto, and the mixture was stirred at room temperature for 15 hr. The reaction mixture was diluted with water and was extracted with ethyl acetate. The organic layer was washed with saturated brine and was dried over anhydrous sodium sulfate, and the filtrate was removed by distillation under reduced pressure. The residue was chromatographed on silica gel column (hexane:ethyl acetate=95:5) to give the title compound as an oil (4.0 g, yield 95%).

1H-NMR (400 MHz, CDCl$_3$): δ (ppm) 7.38-7.30 (m, 5H), 7.03 (d, J=8.4 Hz, 2H), 6.74 (d, J=8.8 Hz, 2H), 5.11 (s, 2H), 2.90 (t, J=8.4 Hz, 2H), 2.65 (t, J=8.4 Hz, 2H), 0.98 (s, 9H), 0.18 (s, 6H); MS (ESI): m/z 369 (M−H)$^+$.

Step 3: Dibenzyl 3-(4-((tert-butyldimethylsilyl)oxy)benzyl)-2-(cis-4-((tert-butyldimethylsilyl)oxy)cyclohexyl)-2-hydroxysuccinate A 2.5 M n-butyllithium solution in hexane (0.49 ml, 1.22 mmol) was added to a solution of diisopropylamine (0.18 ml, 1.29 mmol) in anhydrous THF (3.0 ml) at −78° C. under an argon stream. The mixture was brought to 0° C., and the mixture was stirred for 30 min and was again cooled to −78° C. A solution of benzyl 3-(4-((tert-butyldimethylsilyl)oxy)phenyl)propanoate (300 mg, 0.81 mmol) in anhydrous THF (4.0 ml) was added dropwise thereto at −78° C., and the mixture was stirred for additional one hr. A solution of benzyl 2-(cis-4-((tert-butyldimethylsilyl)oxy)cyclohexyl)-2-oxoacetate (304 mg, 0.81 mmol) in anhydrous THF (4.0 ml) that had been cooled to −78° C. was added through a cannula to the resultant enolate solution over 10 min. The mixture was stirred at −78° C. for one hr, was quenched and adjusted to pH 4 with acetic acid and was allowed to cool to room temperature. The reaction solvent was removed by distillation under reduced pressure, and the residue was diluted with ethyl acetate, and the diluted solution was washed with water and saturated brine and was dried over anhydrous magnesium sulfate. The filtrate was concentrated under reduced pressure. The residue was chromatographed on silica gel column (hexane:ethyl acetate=95:5) to give the title compound as an oil (a diastereomeric mixture; 120 mg, yield 19%).

Low polar diastereomer: 1H-NMR (400 MHz, CDCl$_3$): δ (ppm) 7.32-7.25 (m, 6H), 7.05-7.02 (m, 4H), 6.74-6.69 (m, 4H), 5.05 (d, J=12 Hz, 1H), 4.99 (d, J=12 Hz, 1H), 4.87 (d, J=12 Hz 1H), 4.74 (d, J=12 Hz, 1H), 3.95 (br s, 1H), 3.84 (s, 1H), 3.39-3.35 (m, 1H), 2.98-2.93 (m, 3H), 1.80-1.66 (m, 4H), 1.43-1.28 (m, 4H), 0.98 (s, 9H), 0.88 (s, 9H), 0.08 (s, 6H), 0.02 (s, 6H); MS (ESI): m/z 747 (M$^+$).

High polar diastereomer: $^1$H-NMR (400 MHz, CDCl$_3$): δ (ppm) 7.44-7.36 (m, 6H), 7.10-7.07 (m, 4H), 6.86-6.84 (m, 2H), 6.39-6.64 (m, 2H), 5.33 (d, J=12 Hz, 1H), 5.15 (d, J=12 Hz, 1H), 5.00 (d, J=12 Hz, 1H), 4.68 (d, J=12 Hz, 1H), 3.90 (br s, 1H), 3.61 (s, 1H), 3.34-3.30 (m, 1H), 3.10-2.95 (m, 2H), 2.67-2.62 (m, 1H), 1.78-1.61 (m, 4H), 1.28-1.12 (m, 4H), 1.00 (s, 9H), 0.86 (s, 9H), 0.18 (s, 6H), 0.01 (s, 6H); MS (ESI): m/z 747 (M$^+$).

Step 4: 3-(4-((tert-Butyldimethylsilyl)oxy)benzyl)-2-(cis-4-((tert-butyldimethylsilyl)oxy)cyclohexyl)-2-hydroxysuccinic acid To a solution of dibenzyl 3-(4-((tert-butyldimethylsilyl)oxy)benzyl)-2-(cis-4-((tert-butyldimethylsilyl)oxy)-cyclohexyl)-2-hydroxysuccinate (120 mg, 0.16 mmol) was added 10% Pd-carbon (25 mg) under a nitrogen gas stream. The atmosphere in the reaction vessel was replaced five times with nitrogen gas, the reaction vessel was filled with hydrogen gas, and the system was stirred under a hydrogen gas stream for 24 hr. The mixture was filtered through Celite pad, and the catalyst was washed with ethanol (10 ml×2). The filtrate was concentrated under reduced pressure to give the title compound as an oil (90 mg, yield 99%).

1H-NMR (400 MHz, DMSO-D6): δ (ppm) 12.97 (br s, 1H), 12.08 (br s, 1H), 7.08-6.98 (m, 2H), 6.75-6.72 (m, 2H), 4.53 (br s, 1H), 3.96 (br s, 1H), 2.98-2.80 (m, 3H), 1.66-1.63 (m, 4H), 1.42-1.23 (m, 4H), 0.93 (s, 9H), 0.84 (s, 9H), 0.15 (s, 6H), 0.01 (s, 6H); MS (ESI): m/z 566 ($M^+$).

Step 5: 3-(4-((tert-Butyldimethylsilyl)oxy)benzyl)-4-(cis-4-((tert-butyldimethylsilyl)oxy)cyclohexyl)furan-2,5-dione 3-(4-((tert-Butyldimethylsilyl)oxy)benzyl)-2-(cis-4-((tert-butyldimethylsilyl)oxy)cyclohexyl)-2-hydroxysuccinic acid (90 mg, 0.16 mmol) was dissolved in acetic anhydride (2.0 ml), and the mixture was stirred at 120° C. for 18 hr. The mixture was allowed to cool, excess acetic anhydride was concentrated under reduced pressure, and the residue was chromatographed on silica gel column (hexane:ethyl acetate=94:6) to give the title compound as a yellow oil (60 mg, yield 70%).

1H-NMR (400 MHz, CDCl$_3$): δ (ppm) 7.08 (d, J=8.4 Hz, 2H), 6.76 (d, J=8.4 Hz, 2H), 4.05 (br s, 1H), 3.77 (s, 2H), 2.70-2.64 (m, 1H), 2.26-2.18 (m, 2H), 1.78-1.71 (m, 2H), 1.48-1.36 (m, 4H), 0.97 (s, 9H), 0.91 (s, 9H), 0.18 (s, 6H), 0.06 (s, 6H); MS (ESI): m/z 529 $(M-H)^+$.

Step 6: Dimethyl 2-(4-((tert-butyldimethylsilyl)oxy)benzyl)-3-(cis-4-((tert-butyldimethylsilyl)oxy)cyclohexyl)maleate A 2.0 M trimethylsilyldiazomethane solution in ether (0.43 ml, 0.85 mmol) was added to a solution of 3-(4-((tert-butyldimethylsilyl)oxy)benzyl)-4-(cis-4-((tert-butyldimethylsilyl)oxy)cyclohexyl)furan-2,5-dione (60 mg, 0.11 mmol) in methanol (1.5 ml) at room temperature. The mixture was stirred at room temperature for 5 hr, and the solvent was removed by distillation under reduced pressure. The residue was chromatographed on silica gel column (hexane:ethyl acetate=93:7) to give the title compound as a yellow oil (55 mg, yield 85%).

1H-NMR (400 MHz, CDCl$_3$): δ (ppm) 7.01 (d, J=8.4 Hz, 2H), 6.73 (d, J=8.4 Hz, 2H), 3.96 (br s, 1H), 3.79 (s, 2H), 3.67 (s, 3H), 3.63 (s, 3H), 2.62-2.56 (m, 1H), 1.92-1.82 (m, 2H), 1.68-1.66 (m, 2H), 1.42-1.26 (m, 4H), 0.96 (s, 9H), 0.88 (s, 9H), 0.17 (s, 6H), 0.01 (s, 6H); MS (ESI): m/z 577 ($M^+$).

Step 7: Dimethyl 2-(cis-4-((tert-butyldimethylsilyl)oxy)cyclohexyl)-3-(4-hydroxybenzyl)maleate A 1.0 M tetrabutyl ammonium fluoride solution in THF (0.29 ml, 0.29 mmol) was added dropwise to a solution of dimethyl 2-(4-((tert-butyldimethylsilyl)oxy)benzyl)-3-(cis-4-((tert-butyldimethylsilyl)oxy)cyclohexyl)maleate (55 mg, 0.10 mmol) in THF (1.0 ml) at 0° C., and the mixture was stirred at room temperature for 5 hr. The solvent was removed by distillation under reduced pressure, and the residue was chromatographed on silica gel column (hexane:ethyl acetate=85:15) to give the title compound as a yellow oil (35 mg, yield 80%).

1H-NMR (400 MHz, CDCl$_3$): δ (ppm) 7.02 (d, J=8.8 Hz, 2H), 6.72 (d, J=8.8 Hz, 2H), 4.72 (s, 1H), 3.96 (br s, 1H), 3.79 (s, 3H), 3.66 (s, 2H), 3.62 (s, 3H), 2.64-2.51 (m, 1H), 1.92-1.83 (m, 2H), 1.69-1.66 (m, 2H), 1.39-1.21 (m, 4H), 0.88 (s, 9H), 0.11 (s, 6H); MS (ESI): m/z 461 $(M-H)^+$.

Step 8: Dimethyl 2-(4-(2-((tert-butoxycarbonyl)amino)ethoxy)benzyl)-3-(cis-4-((tert-butyldimethylsilyl)oxy)cyclohexyl)maleate A suspension of dimethyl 2-(cis-4-((tert-butyldimethylsilyl)oxy)cyclohexyl)-3-(4-hydroxybenzyl)maleate (35 mg, 0.075 mmol) and cesium carbonate (27 mg, 0.083 mmol) in DMF (1.2 ml) was cooled to 0° C., a solution of tert-butyl (2-bromoethyl)carbamate (20 mg, 0.091 mmol) in DMF (0.5 ml) was added dropwise, and the mixture was stirred at room temperature for 19 hr. The reaction mixture was diluted with water and was extracted with ethyl acetate, the organic layer was washed with saturated brine and was dried over anhydrous sodium sulfate, and the filtrate was removed by distillation under reduced pressure. The residue was chromatographed on silica gel column (hexane:ethyl acetate=8:2) to give the title compound as an oil (20 mg, yield 43%).

1H-NMR (400 MHz, CDCl$_3$): δ (ppm) 7.07 (d, J=8.4 Hz, 2H), 6.77 (d, J=8.4 Hz, 2H), 3.99-3.97 (m, 3H), 3.79 (s, 3H), 3.68 (s, 2H), 3.63 (s, 3H), 3.52-3.50 (m, 2H), 2.62-2.56 (m, 1H), 1.93-1.84 (m, 2H), 1.70-1.67 (m, 2H), 1.45 (s, 9H), 1.45-1.26 (m, 4H), 0.88 (s, 9H), 0.01 (s, 6H); MS (ESI): m/z 605 $(M-H)^+$.

Step 9: Dimethyl 2-(4-(2-aminoethoxy)benzyl)-3-(cis-4-hydroxycyclohexyl)maleate Concentrated hydrochloric acid (catalytic amount) was added to a solution of dimethyl 2-(4-(2-((tert-butoxycarbonyl)amino)ethoxy)benzyl)-3-(cis-4-((tert-butyldimethylsilyl)oxy)cyclohexyl)maleate (20 mg, 0.033 mmol) in ethanol (1.0 ml) at room temperature, and the mixture was stirred at 50° C. for 15 hr. This mixture was concentrated, and sodium bicarbonate water was added to the residue, followed by extraction with dichloromethane. The organic layer was washed with water and saturated brine and was dried over anhydrous magnesium sulfate, and the filtrate was concentrated. The residue was chromatographed on silica gel column (methanol:dichloromethane=1:9) to give the title compound as an oil (10 mg, yield 83%).

1H-NMR (400 MHz, CDCl$_3$): δ (ppm) 7.04 (d, J=8.4 Hz, 2H), 6.80 (d, J=8.4 Hz, 2H), 3.97-3.96 (m, 2H), 3.95 (br s, 1H), 3.66 (s, 3H), 3.62 (s, 2H), 3.53 (s, 3H), 3.02-3.01 (m, 2H), 2.64-2.58 (m, 1H), 1.76-1.67 (m, 2H), 1.43-1.37 (m, 2H), 1.26-1.19 (m, 4H); MS (ESI): m/z 392 $(M+H)^+$.

Step 10: Disodium 2-(4-(2-aminoethoxy)benzyl)-3-(cis-4-hydroxycyclohexyl)maleate To a solution of dimethyl 2-(4-(2-aminoethoxy)benzyl)-3-(cis-4-hydroxycyclohexyl)maleate 12 mg, 0.03 mmol) in 1,4-dioxane (0.5 ml) was added 1 M NaOH (0.06 ml, 0.06 mmol) at room temperature, and the mixture was stirred at 50° C. for 24 hr. The reaction mixture was concentrated, and the residue was dried in vacuo to give the title compound as a colorless solid (12 mg, quantitative).

1H-NMR (400 MHz, D2O): δ (ppm) 7.20 (d, J=8.0 Hz, 2H), 6.92 (d, J=8.0 Hz, 2H), 4.02-3.98 (m, 3H), 3.58 (s, 2H), 2.92 (br s, 2H), 2.51-2.49 (m, 1H), 1.75-1.25 (m, 8H) MS (ESI): m/z 363 (M−2Na)$^+$.

Example 1

Identification of Inhibitory Activity

Preparation of NDM-1 Enzyme

Amplification was carried out by a polymerase chain reaction (PCR) with Pyrobest DNA polymerase (Takara Bio) in which a plasmid having an NDM-1 gene sequence (GenBank Accession number: FN396876) synthesized by Life Technologies Japan Ltd. (consignment synthesis) was used as a template and two primers (ATACCATGGGTGAAATCCGC-CCGACG and GTGCTCGAGTCAGCGCAGCTTGTCGG) were used. The amplified DNA fragments were digested with restriction enzymes Nco I and Xho I and were incorporated in a vector pET-28a(+) to acquire a recombinant plasmid. The plasmid was transformed into *E. coli* BL21(DE3) (Novagen), and the transformants thus obtained were grown to an absorbance at 600 nm of about 0.7 in 0.8 L of an SB medium (1.2% (w/v) bacto tryptone, 2.4% (w/v) yeast extract, 0.5% (v/v) glycerol, 0.072 M dipotassium hydrogenphosphate, and 0.028 M potassium dihydrogenphosphate) containing 30 μg/ml kanamycin. Isopropyl-β-D-thiogalactopyranoside was added to a final concentration of 1 mM, and induction was carried out at 20° C. overnight, followed by harvesting with a centrifuge. NDM-1 was purified from a cell extract of NDM-1 expressing *E. coli* through an anion exchange column (HiTrap Q HP, GE Health Care Japan) and a hydrophobic interaction column (RESOURCE 15PHE, GE Health Care Japan).

(Measurement of Enzyme Activity)

50 mM HEPES (pH 7.5), 20 μg/ml BSA, 100 μM ZnSO$_4$, 2% DMSO, and 100 μM imipenem as a substrate (these concentrations being final concentration) were added into a 1 ml quartz cell. NDM-1 was added into a quartz cell to a final concentration of 2.5 nM, and the mixture was stirred for an enzyme reaction at 30° C. for 30 sec. Absorbance at 300 nm was measured with UV-2400PC(SHIMADZU) to determine the degradation of the substrate, and the enzyme activity was determined from a change in absorbance when the inhibitor (compounds of Examples 1 to 41) was added. A plurality of inhibitor concentrations were studied, a sigmoid curve was prepared from each inhibitory activity, and IC$_{50}$ values were calculated.

TABLE 1

| Example | Structure | IC$_{50}$ (μM) |
|---|---|---|
| 1 | (CH$_3$)$_2$C=C(CH$_3$)$_2$ substituted with NaO$_2$C, CO$_2$Na | C |
| 2 | Diethyl-substituted alkene with NaO$_2$C, CO$_2$Na | B |
| 3 | Isopropyl/benzyl-substituted alkene with NaO$_2$C, CO$_2$Na | B |
| 4 | Ethyl/methyl/benzyl-substituted alkene with NaO$_2$C, CO$_2$Na | B |
| 5 | Ethyl/methyl/(4-hydroxybenzyl)-substituted alkene with NaO$_2$C, CO$_2$Na | A |
| 6 | Dibenzyl-substituted alkene with NaO$_2$C, CO$_2$Na | A |
| 7 | Benzyl/phenethyl-substituted alkene with NaO$_2$C, CO$_2$Na | A |
| 8 | Diphenethyl-substituted alkene with NaO$_2$C, CO$_2$Na | A |
| 9 | Diisopropyl-substituted alkene with NaO$_2$C, CO$_2$Na | C |
| 10 | Ethyl/isopropyl-substituted alkene with NaO$_2$C, CO$_2$Na | B |
| 11 | Diisopropyl-substituted alkene with NaO$_2$C, CO$_2$Na | B |
| 12 | Isopropyl/benzyl-substituted alkene with NaO$_2$C, CO$_2$Na | B |

TABLE 1-continued

| Example | Structure | IC$_{50}$ (μM) |
|---|---|---|
| 13 | (isopropyl, CH$_2$-(2-methylphenyl), NaO$_2$C, CO$_2$Na on alkene) | B |
| 14 | (ethyl, cyclopentyl, NaO$_2$C, CO$_2$Na on alkene) | A |
| 15 | (isopropyl, cyclopentyl, NaO$_2$C, CO$_2$Na on alkene) | A |
| 16 | (cyclopentyl, CH$_2$-phenyl, NaO$_2$C, CO$_2$Na on alkene) | A |
| 17 | (cyclopentyl, cyclopentyl, NaO$_2$C, CO$_2$Na on alkene) | A |
| 18 | (isopropyl, indan-2-yl, NaO$_2$C, CO$_2$Na on alkene) | A |
| 19 | (isopropyl, cyclohexyl, NaO$_2$C, CO$_2$Na on alkene) | A |
| 20 | (isopropyl, trans-4-hydroxycyclohexyl, NaO$_2$C, CO$_2$Na on alkene) | C |

TABLE 1-continued

| Example | Structure | IC$_{50}$ (μM) |
|---|---|---|
| 21 | (isopropyl, cis-4-hydroxycyclohexyl, NaO$_2$C, CO$_2$Na on alkene) | A |
| 22 | (isopropyl, tetrahydropyran-4-yl, NaO$_2$C, CO$_2$Na on alkene) | B |

TABLE 2

| Example | Structure | IC$_{50}$ (μM) |
|---|---|---|
| 23 | (isopropyl, CH$_2$-pyridin-3-yl, NaO$_2$C, CO$_2$Na on alkene) | C |
| 24 | (ethyl, S-isopropyl, NaO$_2$C, CO$_2$Na on alkene) | C |
| 25 | (isopropyl, CH$_2$-(4-CO$_2$Na-phenyl), NaO$_2$C, CO$_2$Na on alkene) | B |
| 26 | (isopropyl, CH$_2$-(4-CONH$_2$-phenyl), NaO$_2$C, CO$_2$Na on alkene) | B |
| 27 | (isopropyl, CH$_2$-(4-(morpholine-4-carbonyl)phenyl), NaO$_2$C, CO$_2$Na on alkene) | B |
| 28 | (isopropyl, CH$_2$-(4-(4-hydroxypiperidine-1-carbonyl)phenyl), NaO$_2$C, CO$_2$Na on alkene) | C |

TABLE 2-continued

| Example | Structure | IC$_{50}$ (μM) |
|---|---|---|
| 29 | [structure: isopropyl group, C=C with NaO$_2$C and CO$_2$Na, CH$_2$-phenyl-C(=O)NH-CH$_2$-C(=O)NH$_2$] | A |
| 30 | [structure: isopropyl, C=C(NaO$_2$C)(CO$_2$Na), CH$_2$-phenyl-OMe] | A |
| 31 | [structure: isopropyl, C=C(NaO$_2$C)(CO$_2$Na), CH$_2$-phenyl-ONa] | B |
| 32 | [structure: isopropyl, C=C(NaO$_2$C)(CO$_2$Na), CH$_2$-phenyl-O-CH$_2$-C(=O)ONa] | A |
| 33 | [structure: isopropyl, C=C(NaO$_2$C)(CO$_2$Na), CH$_2$-phenyl-O-CH$_2$-C(=O)NH$_2$] | A |
| 34 | [structure: isopropyl, C=C(NaO$_2$C)(CO$_2$Na), CH$_2$-phenyl-O-CH$_2$CH$_2$-NH$_2$] | A |
| 35 | [structure: isopropyl, C=C(NaO$_2$C)(CO$_2$Na), CH$_2$-phenyl-O-CH$_2$CH$_2$-imidazolyl] | A |
| 36 | [structure: isopropyl, C=C(NaO$_2$C)(CO$_2$Na), CH$_2$-phenyl-O-pyrrolidin-3-yl] | A |
| 37 | [structure: isopropyl, C=C(NaO$_2$C)(CO$_2$Na), CH$_2$-phenyl-O-CH$_2$CH$_2$-NH-C(=NH)NH$_2$] | C |
| 38 | [structure: cyclopentyl-C=C(NaO$_2$C)(CO$_2$Na)-cyclohexyl-OH] | A |
| 39 | [structure: HO-cyclohexyl-C=C(NaO$_2$C)(CO$_2$Na)-cyclohexyl-OH] | A |
| 40 | [structure: tetrahydropyranyl-C=C(NaO$_2$C)(CO$_2$Na)-tetrahydropyranyl] | C |
| 41 | [structure: H$_2$N-CH$_2$CH$_2$-O-phenyl-CH$_2$-C=C(NaO$_2$C)(CO$_2$Na)-cyclohexyl-OH] | A |

IC$_{50}$ value:
A = IC$_{50}$: less than 10 μM
B = IC$_{50}$: 10 μM to 30 μM (exclusive)
C = IC$_{50}$: 30 μM to 100 μM (exclusive)

Example 2

Identification of Effect Attained by Combined Use

Effect attained by combined use of compound of Examples 1 to 41 and β-lactam antibiotic in NDM-1 producing *E. coli* was identified by the following method.

A plasmid having an NDM-1 gene sequence (GenBank Accession number: FN396876) that had been synthesized by Life Technologies Japan Ltd. (consignment synthesis) was digested with restriction enzymes EcoRI and PstI, was incorporated in a vector pHSG398 (Takara Bio) to acquire a recombinant plasmid. The plasmid was transformed into *E. coli* DH10B (Invitrogen) to obtain NDM-1-producing *E. coli*, Imipenem, meropenem, doripenem, biapenem, cefepime, and piperacillin were used as β-lactam antibiotics, and the minimum inhibitory centration (MIC) was measured by a broth micro dilution method established by CLSI (Clinical and Laboratory Standards Institute. 2012: Methods for dilution antimicrobial susceptibility tests for bacteria that grow aerobically; approved standard-ninth edition M07-A9. Clinical and Laboratory Standards Institute, Wayne, Pa.). That is, NDM-1-producing *E. coli* that had been cultured overnight in a cation-adjusted Mueller-Hinton broth (Becton Dickinson and Company) was adjusted in the medium so that the concentration was about $10^4$ CFU/well. The adjusted NDM-1-producing *E. coli* was added to the medium containing a β-lactam antibiotic having individual concentrations (64 to 0.031 μg/ml for imipenem, meropenem, doripenem, and biapenem, 256 to 0.125 μg/ml for cefepime, and 1024 to 0.5 μg/ml for piperacillin). The inhibitor was added to each well to a final concentration of 32 μg/ml, the mixture was cultured overnight, and MIC of the β-lactam antibiotic was determined to determine a change in MIC derived from the combined use of the compound and the inhibitor.

As a result, it was confirmed that all the compounds restored the antimicrobial activity of the β-lactam antibiotic by a factor of 2 to 256.

INDUSTRIAL APPLICABILITY

The inhibition of NDM-1 by compounds of general formula (I) according to the present invention suppresses deactivation of the β-lactam antibiotics and can restore the antimicrobial activity thereof.

The invention claimed is:

1. A method of suppressing deactivation of a β-lactam antibiotic, wherein the deactivation of the β-lactam antibiotic is caused by a New Delhi metallo-β-lactamase producing bacteria strain, the method comprising administering a pharmaceutically effective amount of a compound of formula (I), or a salt thereof,

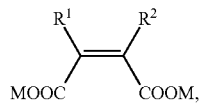

(I)

wherein
$R^1$ represents $C_{1-7}$ alkyl optionally substituted by phenyl or —$OM^1$ wherein $M^1$ represents a hydrogen atom or a pharmaceutically acceptable cation; or tetrahydropyran,
$R^2$ represents $C_{1-7}$ alkyl optionally cyclocondensed with phenyl or optionally substituted by phenyl, pyridyl, or —$OM^1$ wherein $M^1$ represents a hydrogen atom or a pharmaceutically acceptable cation, the phenyl group being optionally substituted by $C_{1-7}$ alkyl, —O—$C_{1-2}$ imidazole, —O-pyrrolidine, —O—$C_{1-2}$—$COOM^2$, —O—$C_{1-2}$—$CONH_2$, —O—$C_{1-2}$—$NH_2$, —O—$C_{1-2}$—NH—C(=NH)—$NH_2$, —O—$C_{1-7}$ alkyl, —$OM^2$, —$COOM^2$, —$CONH_2$, —CO—$NHCH_2CONH_2$, —CO-morpholine, or —CO-piperidine optionally substituted by hydroxyl, wherein $M^2$ represents a hydrogen atom or a pharmaceutically acceptable cation; tetrahydropyran; or —S—$C_{1-7}$ alkyl, and
two M's which may be the same or different represent a hydrogen atom or a pharmaceutically acceptable cation,
to a patient in need thereof.

2. The method according to claim 1, wherein the β-lactam antibiotic is a carbapenem antibiotic, a cephem antibiotic, or a penicillin antibiotic.

3. The method according to claim 1, further comprising administering a dehydropeptidase inhibitor.

4. The method according to claim 1, wherein the compound of formula (I) is selected from the group consisting of:
disodium 2-cyclopentyl-3-(cis-4-hydroxycyclohexyl)maleate;
disodium 2,3-bis(cis-4-hydroxycyclohexyl)maleate;
disodium 2,3-bis(tetrahydro-2H-pyran-4-yl)maleate; and
disodium 2-(4-(2-aminoethoxyl)benzyl)-3-(cis-4-hydroxycyclohexyl)maleate,
or a salt thereof.

5. The method according to claim 1, wherein the New Delhi metallo-β-lactamase bacteria strain is a New Delhi metallo-β-lactamase-1 bacteria strain.

* * * * *